US009463039B2

(12) United States Patent
Kuroda et al.

(10) Patent No.: US 9,463,039 B2
(45) Date of Patent: Oct. 11, 2016

(54) ENDOSCOPIC DEVICE

(71) Applicant: Olympus Corporation, Tokyo (JP)

(72) Inventors: Noriko Kuroda, Tokyo (JP); Kunihide Kaji, Tokyo (JP); Takuo Yokota, Tokyo (JP); Nobuko Matsuo, Tokyo (JP); Takayasu Mikkaichi, Tokyo (JP); Hiroko Sakamoto, Tokyo (JP); Masatoshi Sato, Tokyo (JP); Ryuhei Shimada, Tokyo (JP); Satoko Suzuki, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 19 days.

(21) Appl. No.: 14/305,553

(22) Filed: Jun. 16, 2014

(65) Prior Publication Data

US 2015/0032119 A1     Jan. 29, 2015

Related U.S. Application Data

(63) Continuation of application No. PCT/JP2014/050310, filed on Jan. 10, 2014.

(60) Provisional application No. 61/754,110, filed on Jan. 18, 2013.

(51) Int. Cl.
*A61B 17/24*     (2006.01)
*A61B 17/221*     (2006.01)
(Continued)

(52) U.S. Cl.
CPC ............ *A61B 17/221* (2013.01); *A61B 10/06* (2013.01); *A61B 17/295* (2013.01);
(Continued)

(58) Field of Classification Search
CPC ................ A61B 10/06; A61B 17/221; A61B 2017/2212; A61B 2017/2944; A61B 2017/2938; A61B 17/2932; A61B 17/32056; A61B 17/295
See application file for complete search history.

(56) References Cited

U.S. PATENT DOCUMENTS 5,108,406 A    4/1992   Lee
5,171,314 A *   12/1992   Dulebohn ........ A61B 17/32056
                                                                    606/110

(Continued)

FOREIGN PATENT DOCUMENTS

JP       A-8-38497       2/1996
JP       A-2000-51229       2/2000

(Continued)

OTHER PUBLICATIONS

Aug. 12, 2014 Office Action issued in Japanese Application No. 2014-528357 (with translation).

(Continued)

*Primary Examiner* — Corrine McDermott
*Assistant Examiner* — Sarah Simpson
(74) *Attorney, Agent, or Firm* — Oliff PLC

(57) ABSTRACT

An endoscopic device includes a longitudinal member, a pair of jaws installed at a distal end of the longitudinal member and configured to be freely opened and closed, a first grasping member supported by a first jaw of the pair of jaws, a second grasping member supported by a second jaw of the pair of jaws, the second body having a wire shape, flexibility, and being curved in a loop shape, a long operating transmission member having a distal end portion connected to the pair of jaws and installed to advance and retreat along a longitudinal axis of the longitudinal member, and an open-close operating portion installed at a proximal end portion of the operating transmission member and configured to be manipulated to open and close the pair of jaws.

19 Claims, 32 Drawing Sheets

(51) Int. Cl.
- *A61B 17/295* (2006.01)
- *A61B 17/3205* (2006.01)
- *A61B 10/06* (2006.01)
- *A61B 17/00* (2006.01)
- *A61B 17/29* (2006.01)

(52) U.S. Cl.
CPC ............ *A61B 17/32056* (2013.01); *A61B 2017/00353* (2013.01); *A61B 2017/00358* (2013.01); *A61B 2017/2901* (2013.01); *A61B 2017/2923* (2013.01); *A61B 2017/2926* (2013.01); *A61B 2017/2929* (2013.01)

(56) References Cited

U.S. PATENT DOCUMENTS

| | | | | |
|---|---|---|---|---|
| 5,562,678 | A * | 10/1996 | Booker | A61B 17/29 606/106 |
| 6,440,062 | B1 * | 8/2002 | Ouchi | A61B 1/00098 600/146 |
| 8,092,470 | B2 | 1/2012 | Miyamoto et al. | |
| 9,039,721 | B2 * | 5/2015 | Ziniti | A61B 17/0485 606/170 |
| 2003/0187457 | A1 | 10/2003 | Weber | |
| 2004/0059345 | A1 * | 3/2004 | Nakao | A61B 17/221 606/113 |
| 2013/0006262 | A1 * | 1/2013 | Lampropoulos | A61B 17/221 606/113 |
| 2013/0317515 | A1 | 11/2013 | Kuroda et al. | |

FOREIGN PATENT DOCUMENTS

| | | |
|---|---|---|
| JP | A-2005-160648 | 6/2005 |
| JP | A-2006-136726 | 6/2006 |
| JP | A-2006-517444 | 7/2006 |
| JP | A-2009-529983 | 8/2009 |
| JP | A-2012-101121 | 5/2012 |
| WO | WO 2004/069025 A2 | 8/2004 |
| WO | WO 2007/106813 A2 | 9/2007 |

OTHER PUBLICATIONS

International Search Report issued in International Patent Application No. PCT/JP2014/050310 mailed on Feb. 25, 2014 (with translation).

Jul. 13, 2016 Office Action issued in Chinese Patent Application No. 201480002432.4.

\* cited by examiner

ENDOSCOPIC DEVICE

The present application is a Continuation of International Patent Application No. PCT/JP2014/050310, filed Jan. 10, 2014, claiming priority on U.S. Provisional Patent Application No. 61/754,110, filed Jan. 18, 2013, the contents of both of Provisional Application and PCT International Patent Application are incorporated herein by reference.

BACKGROUND OF THE INVENTION

1. Field of the Invention

The present invention relates to an endoscopic device.

2. Description of Related Art

In the related art, a procedure of endoscopically excising a lesion or the like is known. As an endoscopic device used in such a procedure, an endoscopic device used with an endoscope apparatus in order to collect the excised lesion or the like is known.

For example, in Japanese Unexamined Patent Application, First Publication No. 2005-160648, a wire for removing foreign substances in a blood vessel which includes two loop-shaped sandwiching portions formed at a distal end side of an elongated wire main body having flexibility is disclosed. In the wire for removing foreign substances in the blood vessel disclosed in Japanese Unexamined Patent Application, First Publication No. 2005-160648, the foreign substances in the blood vessel can be sandwiched and collected by being reduced the distance between the sandwiching portions by moving the two loop-shaped sandwiching portions relative to each other.

In Japanese Unexamined Patent Application, First Publication No. 2006-136726, a tissue ablation apparatus configured to advance or retreat an exfoliation loop and a cutting loop with respect to a probe is disclosed. In the tissue ablation apparatus disclosed in Japanese Unexamined Patent Application, First Publication No. 2006-136726, the exfoliation loop and the cutting loop can be moved between a receiving position and an open position.

SUMMARY OF THE INVENTION

An endoscopic device according to a first aspect of the present invention includes a longitudinal member having a longitudinal axis; a pair of jaws installed at a distal end of the longitudinal member and configured to be freely opened and closed; a first grasping member supported by a first jaw of the pair of jaws; a second grasping member supported by a second jaw of the pair of jaws, the second grasping member having a wire shape, flexibility, and being curved in a loop shape; a long operating transmission member having a distal end portion connected to the pair of jaws and installed to be movable along the longitudinal axis of the longitudinal member; and an open-close operating portion installed at a proximal end portion of the operating transmission member and configured to be manipulated to open and close the pair of jaws and add to or release a grasping force of grasping an object to be grasped between the first grasping member and the second grasping member.

According to a second aspect of the present invention, in the endoscopic device according to the first aspect, the first grasping member may be supported by the first jaw so as to be capable of protruding from the first jaw, the second grasping member may be supported by the second jaw so as to be capable of protruding from the second jaw, and the second grasping member may have an elastic force forming the loop shape upon protrusion from the second jaw.

According to a third aspect of the present invention, in the endoscopic device according to the second aspect, a distal end opening portion configured to accommodate the second grasping member may be formed at a distal end surface of the second jaw.

According to a fourth aspect of the present invention, in the endoscopic device according to the first aspect, the second grasping member may be curved in the loop shape within a plane crossing an open-close direction of the pair of jaws.

According to a fifth aspect of the present invention, in the endoscopic device according to the first aspect, wherein the first grasping member may have a wire shape, flexibility, and being curved in the loop shape, the second grasping member may be installed so as to be capable of varying a grasping area of the loop shape within a plane crossing the open-close direction of the jaws, the longitudinal member may be tubular, and the operating transmission member may be installed inside the longitudinal member.

According to a sixth aspect of the present invention, in the endoscopic device according to the fifth aspect, the second grasping member may be installed so as to advance in a direction protruding from the jaws and to retreat in a direction accommodated in the jaws, and the second grasping member may be installed so as to be capable of varying the grasping area within the plane crossing the open-close direction of the jaws according to the advance and retreat motion of the second grasping member.

According to a seventh aspect of the present invention, in the endoscopic device according to the fifth aspect, each of the first grasping member and the second grasping member may be installed so as to advance in a direction protruding from the jaws and to retreat in a direction accommodated in the jaws, and the first grasping member and the second grasping member may be installed so as to be capable of independently varying the grasping area within the plane crossing the open-close direction of the jaws according to the advance and retreat motion of the first grasping member and the second grasping member.

According to an eighth aspect of the present invention, in the endoscopic device according to the fifth aspect, when the first grasping member and the second grasping member are closed, the first grasping member may be set to incline to inside of the pair of jaws.

According to a ninth aspect of the present invention, in the endoscopic device according to the fourth aspect, the first grasping member may have a wire shape, flexibility, and being curved in the loop shape, and when the first grasping member and the second grasping member are closed, the first grasping member and the second grasping member may be inclined to inside of the pair of jaws, and one of the first grasping member and the second grasping member may be set to enter a space inside of the loop shape of the other grasping member.

According to a tenth aspect of the present invention, in the endoscopic device according to the fourth aspect, the first grasping member may have a wire shape, flexibility, and being curved in the loop shape, the first grasping member and the second grasping member may have main wires formed in the loop shape, and auxiliary wires formed in the loop shape having a smaller grasping area than that of the main wire and disposed inside the main wire at intervals, and the grasping area of the loop shape of the auxiliary wire of the first grasping member and the grasping area of the loop shape of the auxiliary wire of the second grasping member may be different from each other.

According to an eleventh aspect of the present invention, in the endoscopic device according to the tenth aspect, a centerline of the main wire connecting between a point where the main wire supported by the jaws and a point where maximally spaced apart from the jaws, and a centerline of the auxiliary wire connecting between a point where the auxiliary wire supported by the jaws and a point where maximally spaced apart from the jaw may be positioned so as to overlap in the same plane including both of the main wire and the auxiliary wire.

According to a twelfth aspect of the present invention, in the endoscopic device according to the tenth aspect, a centerline of the main wire connecting between a point where the main wire supported by the jaws and a point where maximally spaced apart from the jaws, and a centerline of the auxiliary wire connecting between a point where the auxiliary wire supported by the jaws and a point where maximally spaced apart from the jaws may be deviated from each other when seen in a direction perpendicular to a plane including the main wire.

According to a thirteenth aspect of the present invention, in the endoscopic device according to the tenth aspect, the main wire and the auxiliary wire may be set to be inclined toward further inside positions than positions of the pair of jaws when the first grasping member and the second grasping member are closed.

According to a fourteenth aspect of the present invention, in the endoscopic device according to the tenth aspect, the main wire and the auxiliary wire curved in a loop shape may be inclined toward a further inside position than the positions of the pair of jaws when the first grasping member and the second grasping member are closed, and at least one of the main wire and the auxiliary wire that constitute the first grasping member of the first grasping member and the second grasping member may be set to enter a space inside the loop shape of at least one of the main wire and the auxiliary wire of the second grasping member.

According to a fifteenth aspect of the present invention, in the endoscopic device according to the fourth aspect, the first grasping member and the second grasping member may be constituted by a wire having flexibility and being curved, both ends of the wire may be inserted through two throughholes formed in the distal end surfaces of the jaws to extend toward the longitudinal member, the wire may be installed so as to advance in a direction protruding from the jaws and to retract in a direction accommodated in the jaws, and the wires of the first grasping member and the second grasping member may be installed so as to be capable of independently advancing and retreating with respect to each of the jaws, and the wires curved and formed in the loop shape may be installed so as to be capable of independently varying the grasping areas of the loop shapes within a plane crossing the open-close direction of the pair of jaws according to the advance and retreat motion of the wires.

According to a sixteenth aspect of the present invention, in the endoscopic device according to the fifteenth aspect, the first grasping member may have a main wire having the loop shape, and have an auxiliary wire having the loop shape with a smaller grasping area than that of the main wire and disposed inside the main wire at an interval.

According to a seventeenth aspect of the present invention, the endoscopic device according to the first aspect may further include an operating portion connected to at least one of the first grasping member and the second grasping member installed at a proximal end of the longitudinal member. The first grasping member may have a wire shape, flexibility, and is curved in the loop shape. The first grasping member may have a main wire having the loop shape; and an auxiliary wire having the loop shape with a relatively smaller grasping area than that of the main wire and disposed inside the main wire at an interval. The operating portion may have a first movable member configured to advance and retract the main wire in a central axis direction of the longitudinal member; and a second movable member configured to advance and retract the auxiliary wire in the central axis direction of the longitudinal member.

According to an eighteenth aspect of the present invention, in the endoscopic device according to the seventeenth aspect, the first movable member may be a first pulley in which the main wire is suspended on an outer circumference thereof. The second movable member may be a second pulley of which the auxiliary wire is suspended on an outer circumference thereof. The first pulley may have a larger diameter than that of the second pulley, and the first pulley and the second pulley may be integrally rotatable about the same rotational center.

According to a nineteenth aspect of the present invention, the endoscopic device according to the eighteenth aspect may further include a rotary shaft concentric with the rotational center and fixed to the first pulley and the second pulley; and a dial installed at a portion of the rotary shaft positioned outside the operating portion and rotated by an operator.

According to a twentieth aspect of the present invention, the endoscopic device according to the eighteenth aspect may further include a pinion connected to the first pulley and the second pulley; a rack meshed with the pinion and disposed in the operating portion; and a slider formed at a portion of the rack, disposed outside the operating portion, and installed to advance and retreat in a lengthwise direction of the rack by an operator.

According to a twenty-first aspect of the present invention, the endoscopic device according to the seventeenth aspect may have a first slider serving as the first movable member, fixed to the main wire, disposed at the operating portion, and configured to advance and retreat in a predetermined direction in the operating portion; a second slider serving as the second movable member, fixed to the auxiliary wire, disposed at the operating portion, and configured to advance and retreat in the predetermined direction; and a stopper installed at the first slider and configured to limit movement of the second slider to the distal end side farther than the first slider. The second slider may be configured to freely advance and retreat in the predetermined direction when the second slider is disposed to be spaced apart from the first slider farther than the proximal end side in the operating portion, and the second slider may be configured to be capable of moving to the proximal end side of the operating portion while abutting the stopper and moving to the distal end side of the operating portion only when moved to the distal end side of the operating portion with the first slider.

DETAILED DESCRIPTION OF THE INVENTION

First Embodiment

Figure 1:
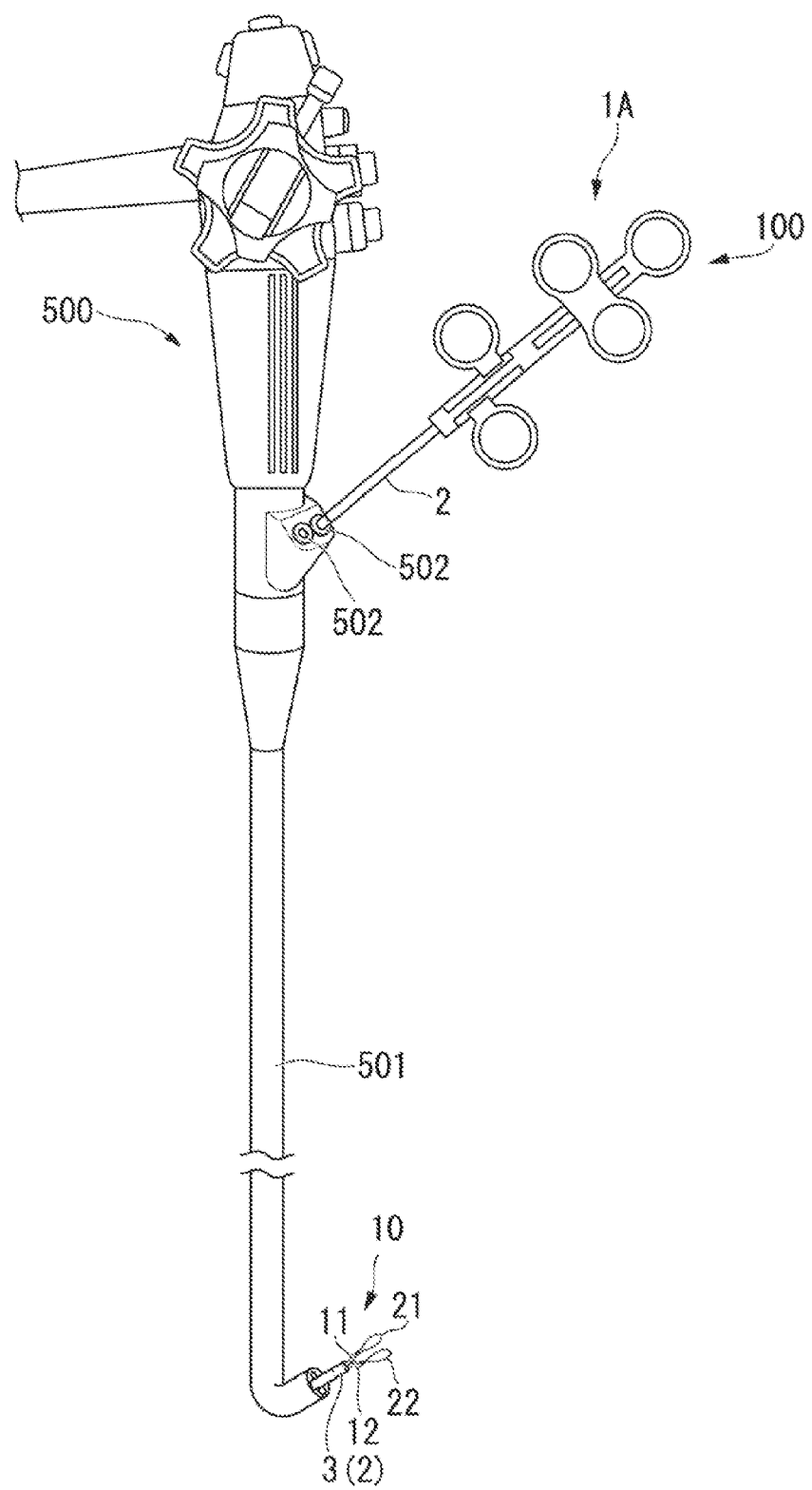
FIG. 1 is an overall view showing an endoscopic device according to a first embodiment of the present invention and an endoscope apparatus used with the endoscopic device.

An endoscopic device according to a first embodiment of the present invention will be described. FIG. 1 is an overall view showing the endoscopic device of the embodiment and an endoscope apparatus 500 used with the endoscopic device.

As shown in FIG. 1, an endoscopic device 1A is an endoscopic device used with the endoscope apparatus 500. A configuration of the endoscope apparatus 500 used with the endoscopic device 1A is not particularly limited. For example, in the embodiment, the endoscope apparatus 500 is a flexible endoscope including a flexible insertion portion 501 inserted into the stomach from the mouth and an endoscope channel 502 configured to be inserted into the endoscopic device 1A and installed in the insertion portion 501.

The endoscopic device 1A includes a treatment portion 10, an insertion portion 2 and an operating portion 100. The treatment portion 10 is used for treatment in the body. The treatment portion 10 is installed at a distal end of the insertion portion 2. The operating portion 100 is installed at a proximal end of the insertion portion 2. The endoscopic device 1A will be described by defining a side at which the treatment portion 10 is installed as a distal end side and a side at which the operating portion 100 is installed as a proximal end side.

The insertion portion 2 is a member inserted into the endoscope channel 502 of the endoscope apparatus 500 such as a flexible endoscope or the like. The insertion portion 2 is inserted into the endoscope channel 502 from the distal end of the insertion portion 2. The insertion portion 2 includes a longitudinal member 3 having a longitudinal axis. The longitudinal member 3 is a tubular member with a distal end side and a proximal end side opened. The longitudinal member 3 has flexibility such that the longitudinal member 3 can advance and retreat in the endoscope channel 502 even when the endoscope channel 502 of the endoscope apparatus 500 is curved.

Figure 2:
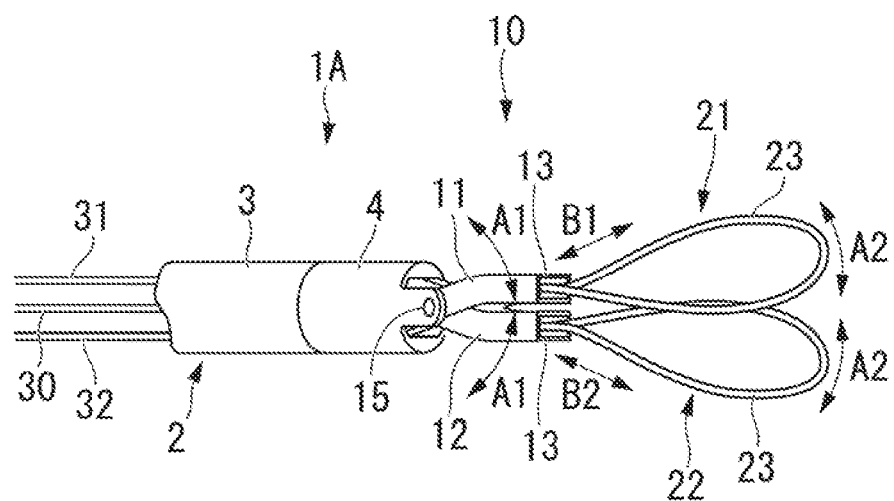
FIG. 2 is a perspective view of a treatment portion of a distal end of the endoscopic device according to the first embodiment of the present invention.
Figure 3:
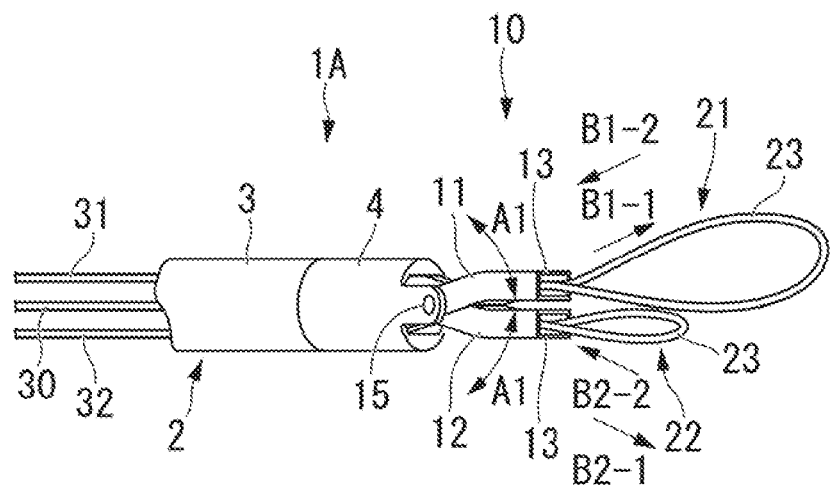
FIG. 3 is a perspective view of the treatment portion of the distal end of the endoscopic device according to the first embodiment of the present invention.
Figure 4:
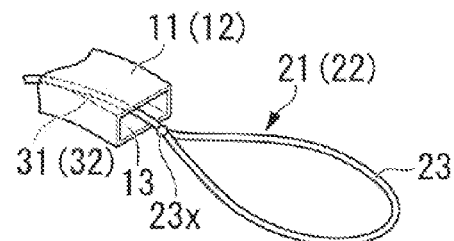
FIG. 4 is a perspective view showing an example of an assembling ways of a wire of the treatment portion of the distal end of the endoscopic device according to the first embodiment of the present invention.

FIGS. 2 and 3 are perspective views of the treatment portion of the distal end of the endoscopic device 1A according to the embodiment.

As shown in FIG. 2, the treatment portion 10 is installed at the distal end of the longitudinal member 3 of the insertion portion 2. A pair of jaws 11 and 12 constituted by a first jaw 11 and a second jaw 12 (which may hereinafter be referred to as "the jaws 11 and 12") are installed at the treatment portion 10. The pair of jaws 11 and 12 are simultaneously opened and closed in an arrow A1 direction crossing a longitudinal axis of the longitudinal member 3. The first jaw 11 and the second jaw 12 are supported at a cylindrical housing 4 fixed to the distal end of the longitudinal member 3. The first jaw 11 and the second jaw 12 are manipulated to be opened and closed by the operating portion 100.

A first grasping member 21 and a second grasping member 22 configured to be opened and closed with the jaws 11 and 12 are installed at the distal end sides of the first jaw 11 and the second jaw 12, respectively. The first grasping member 21 and the second grasping member 22 (which may hereinafter be referred to as "the grasping members 21 and 22") are grasp portions configured to collect a tissue or the like (including a necrotic tissue), which is an object to be grasped such as a lesion area or the like. As shown in FIG. 2, the first grasping member 21 and the second grasping member 22 are opened and closed in an arrow A2 direction, which is the same as the open-close direction of the jaws 11 and 12 shown by the arrow A1. The grasping members 21 and 22 exert a grasping force on a tissue or the like, which is the object to be grasped d, upon closing such that the object to be grasped can be grasped.

The grasping members 21 and 22 include linear members annularly curved within a plane crossing the open-close direction of the jaws 11 and 12 (the arrow A1 direction of FIG. 2). In the embodiment, the grasping members 21 and 22 are constituted by wires 23 having flexibility and curved in a loop shape (hereinafter referred to as "a loop wire").

The loop wires 23 are formed to exit distal end openings (distal end opening portions) 13 of the jaws 11 and 12 to return to the distal end opening 13 of the jaws 11 and 12 while forming a loop similar to a circular or oval shape, or the like. Starting ends and terminating ends of the loop wires 23 are formed to be pulled into the distal end openings 13 of the jaws 11 and 12.

The starting ends and the terminating ends of the loop wires 23 pulled into the distal end openings 13 of the jaws 11 and 12 are coupled to distal ends of advance-retreat manipulation wires 31 and 32, for example, in the jaws 11 and 12. The advance-retreat manipulation wires 31 and 32 are installed to independently advance and retreat along the longitudinal axis of the longitudinal member 3. Accordingly, as the advance-retreat manipulation wires 31 and 32 are manipulated to advance and retreat, the loop wires 23 advance in a direction in which they protrude from the jaws 11 and 12 and retreat in a direction in which they are accommodated in the jaws 11 and 12. In addition, the loop wires 23 are formed such that sizes of the loops in a plane perpendicular to the plane in which the jaws 11 and 12 are opened and closed are enlarged or reduced according to advance and retreat operations of the loop wires 23.

The advance-retreat manipulation wires 31 and 32 are individually installed with respect to the loop wire 23 of the first grasping member 21 of the loop wire 23 of the second grasping member 22. As shown in FIG. 2, the endoscopic device 1A can independently enlarge or reduce the size of the loop by individually advancing and retracting the loop wire 23 of the first grasping member 21 and the loop wire 23 of the second grasping member 22 in arrow B1 and B2 directions.

FIG. 3 shows a state in which the loop wire 23 of the first grasping member 21 protrudes from the jaw 11 to enlarge the loop and the loop wire 23 of the second grasping member 22 is retracted into the jaw 12 to shrink the loop.

As shown in FIG. 3, the endoscopic device 1A having the treatment portion 10 can individually and freely vary the protrusion amount of the loop wires 23 and the sizes of the loops using the first grasping member 21 and the second grasping member 22.

As a material of the loop wires, a metal wire having biocompatibility generally used in the endoscopic device is employed. Specifically, single wires or stranded wires of stainless steel or a super-elastic alloy (NiTi alloy or the like) are used. Diameters of the wires may be within a range of 0.3 mm to 1.0 mm.

FIGS. 4 to 7 are perspective views showing an example of a assembling ways of the wire of the treatment portion. In the example shown in FIG. 4, the starting end and the terminating end of the loop wire 23 are coupled at a tie point 23x. Then, the distal end of the advance-retreat manipulation wire 31 (32) is connected to the tie point 23x.

Figure 5:
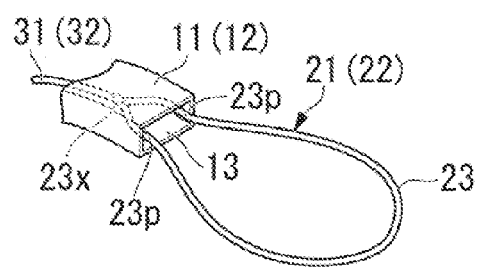
FIG. 5 is a perspective view showing the example of the assembling ways of the wire of the treatment portion of the distal end of the endoscopic device according to the first embodiment of the present invention.

In the example shown in FIG. 5, the tie point 23x of the starting end and the terminating end of the loop wire 23 are formed to remain in the jaw 11 (12) even when the loop wire 23 is maximally pushed out toward the outside of the jaw 11 (12). As a result, as two points 23p and 23p spaced apart from each other at the jaw 11 (12) side of the loop wire 23 abut a wall of the distal end opening 13 of the jaw 11 (12), the loop wire 23 is supported by the jaw 11 (12). Accordingly, the loop wire 23 does not needlessly rotate.

Figure 6:
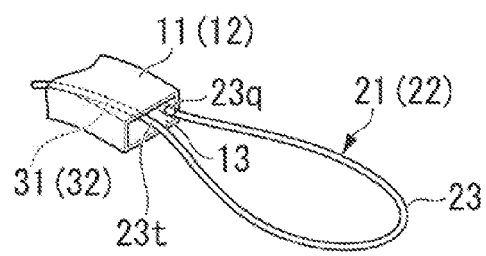
FIG. 6 is a perspective view showing the example of the assembling ways of the wire of the treatment portion of the distal end of the endoscopic device according to the first embodiment of the present invention.

In the example shown in FIG. 6, a starting end 23q of the loop wire 23 is fixed to the wall of the distal end opening 13 of the jaw 11 (12). A terminating end 23t side of the loop wire 23 continues to the advance-retreat manipulation wire 31 (32). Accordingly, the loop wire 23 is installed such that a first end is fixed and a second end is movable. As a result, as the advance-retreat manipulation wire 31 (32) advances or retreats, the loop wire 23 protrudes or retracts from the distal end of the first jaw 11 while increasing or decreasing the size of the loop. In this example, the starting end 23q and the terminating end 23t of the loop wire 23 are spaced from each other at the jaw 11 (12) side, and the starting end 23q and the terminating end 23t are supported by the wall of the distal end opening 13 of the jaw 11 (12). Accordingly, the loop wire 23 does not needlessly rotate.

Figure 7:
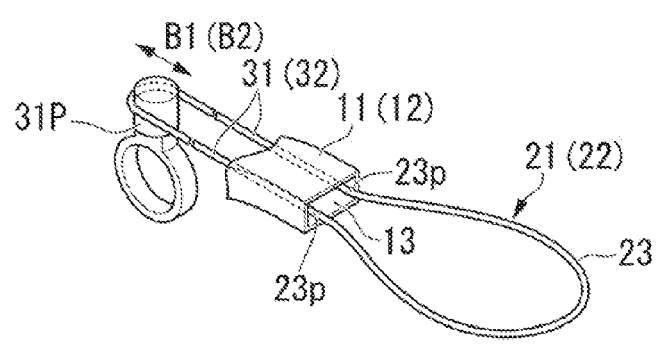
FIG. 7 is a perspective view showing the example of the assembling ways of the wire of the treatment portion of the distal end of the endoscopic device according to the first embodiment of the present invention.

In the example shown in FIG. 7, the starting end and the terminating end of the loop wire 23 are installed to continue to the two advance-retreat manipulation wires 31 (32). Both of proximal ends of the advance-retreat manipulation wire 31 (32) are held by a manipulation member 31P. Accordingly, as the manipulation member 31P advances and retreats in an arrow B1 (B2) direction shown in FIG. 7, the loop wire 23 exits or enters the distal end of the jaw 11 while increasing or decreasing the size of the loop. In this example, the two points 23p and 23p spaced apart from each other at the jaw 11 (12) side of the loop wire 23 abut the wall of the distal end opening 13 of the jaw 11 (12) to be supported. Accordingly, the loop wire 23 does not needlessly rotate.

Figure 8:
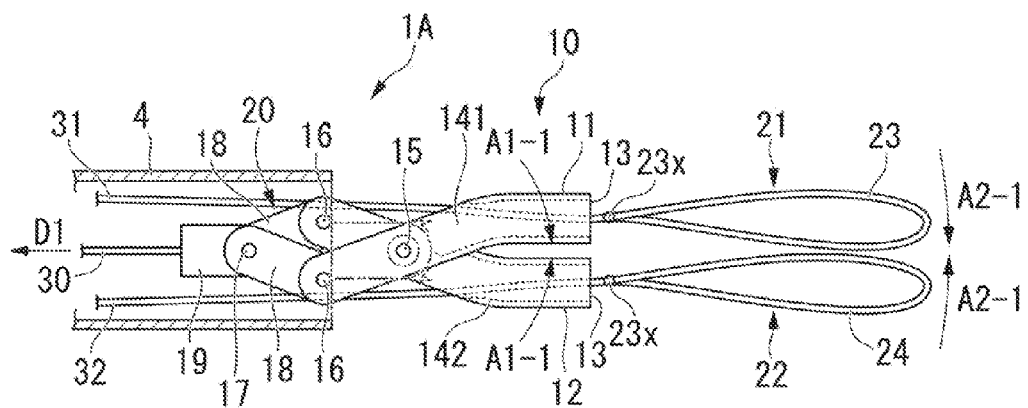
FIG. 8 is a view showing an internal structure of the treatment portion of the distal end of the endoscopic device according to the first embodiment of the present invention.
Figure 9:
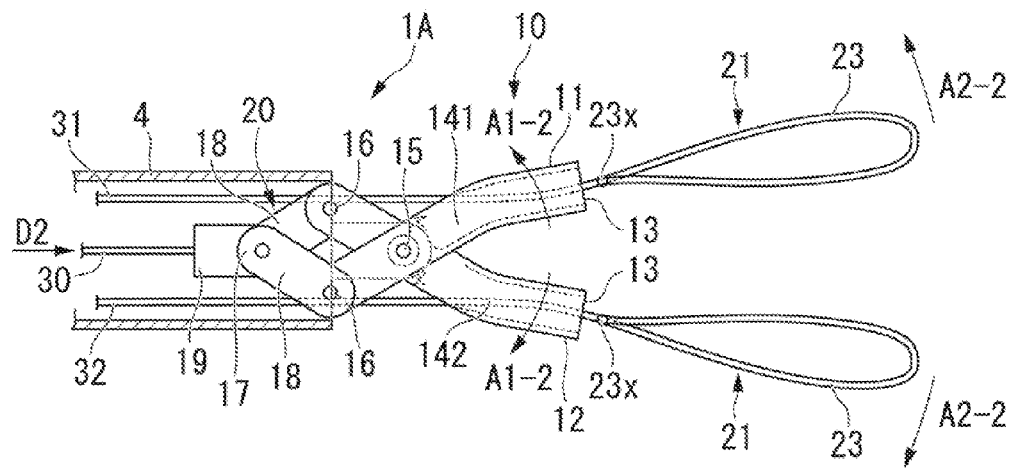
FIG. 9 is a view showing the internal structure of the treatment portion of the distal end of the endoscopic device according to the first embodiment of the present invention.

FIGS. 8 and 9 are cross-sectional view showing an internal structure of the treatment portion 10. FIG. 8 shows a state in which the jaws 11 and 12 are substantially closed. FIG. 9 shows a state in which the jaws 11 and 12 are opened.

As shown in FIGS. 8 and 9, the pair of jaws 11 and 12 have arms 141 and 142 integrally extending from the jaws 11 and 12 at proximal end sides thereof. The arm 141 integrally formed with the first jaw 11 and the arm 142 integrally formed with the second jaw 12 cross in an X shape at an intermediate portion between the distal end and the proximal end that connect the jaws 11 and 12. A fixing pin 15 is installed at a place at which the arm 141 and the arm 142 cross in an X shape. The fixing pin 15 is fixed to the cylindrical housing 4 fixed to the distal end of the longitudinal member 3.

Each of the arms 141 and 142 is rotatably supported by the fixing pin 15. In addition, one end of an intermediate link 18 is rotatably connected to a proximal end of each of the arms 141 and 142 by a pin 16. The other ends of the two intermediate links 18 are rotatably connected to a manipulation block 19 by a pin 17. A distal end of a long open-close manipulation wire (an operating transmission member) 30 is connected to the manipulation block 19. Accordingly, an open-close mechanism 20 of the jaws 11 and 12 is constituted by a four-joint link. That is, the pair of jaws 11 and 12 are configured to be opened and closed as the manipulation block 19 advances and retreats along the longitudinal axis of the longitudinal member 3.

For example, as shown in FIG. 8, when the manipulation block 19 is pulled in a direction shown by an arrow D1, the jaws 11 and 12 are simultaneously displaced in a closing direction (an arrow A1-1 direction). When the jaws 11 and 12 are displaced in the closing direction, the pair of grasping members 21 and 22 are displaced in a closing direction (an arrow A2-1 direction). Meanwhile, as shown in FIG. 9, when the manipulation block 19 is pushed in a direction shown by an arrow D2, the jaws 11 and 12 are simultaneously displaced in an opening direction (an arrow A1-2 direction). When the jaws 11 and 12 are displaced in the opening direction, the pair of grasping members 21 and 22 are displaced in an opening direction (an arrow A2-2 direction).

In FIGS. 8 and 9, although the tie point 23x of the starting end and the terminating end of the loop wire 23 protrudes from the distal end opening 13 of the jaws 11 and 12, the tie point 23x may not exit the distal end opening 13 of the jaws 11 and 12. However, a plane in which the loop of the loop wire 23 is formed (a plane including the loop wire 23) crosses an open-close direction (the arrow A2 direction) of the loop wire 23. In addition, when the two loop wires 23 are manipulated on at least a closed position, there is a need to provide an overlapping portion when seen in the open-close direction. In addition, when the loop wire 23 is contracted at the maximum position, the loop wire 23 is provided so as to be capable of being accommodated in the distal end opening 13 of the jaws 11 and 12.

Figure 10:
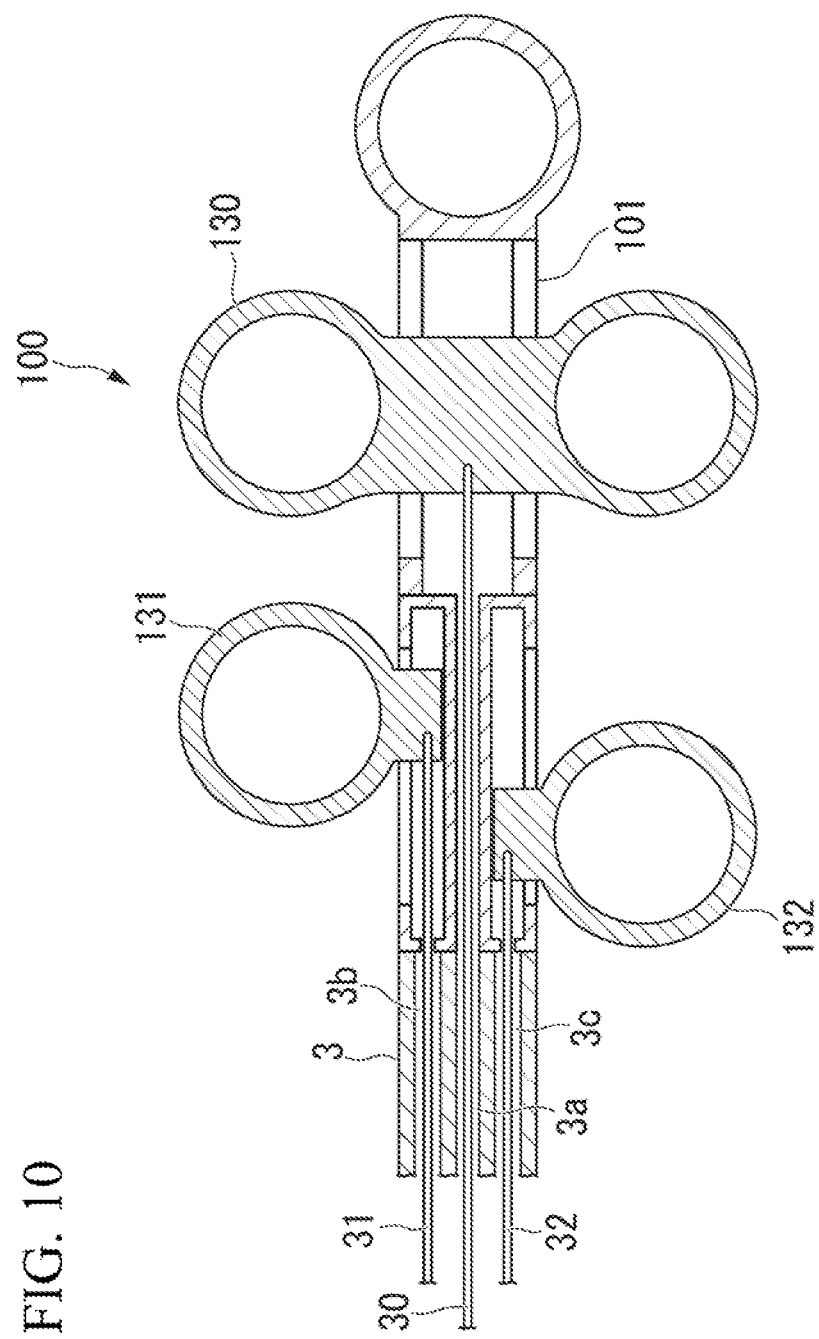
FIG. 10 is a cross-sectional view showing an internal structure of an operating portion of the endoscopic device according to the first embodiment of the present invention.

FIG. 10 is a cross-sectional view showing an internal structure of the operating portion of the endoscopic device according to the embodiment. As shown in FIG. 10, the operating portion 100 of the endoscopic device 1A has an operating portion main body 101, and three manipulation members, i.e., an open-close manipulation member (an open-close operating portion) 130, a first advance-retreat manipulation member 131, and a second advance-retreat manipulation member 132. The three manipulation members 130, 131 and 132 are slidably installed at the operating portion main body 101. A proximal end of the longitudinal member 3 is connected to the operating portion main body 101.

A first lumen 3a through which the open-close manipulation wire 30 is inserted, and two lumens, i.e., a second lumen 3b and a third lumen 3c through which the advance-retreat manipulation wires 31 and 32 are inserted, respectively, are installed at the longitudinal member 3. For example, the three lumens 3a, 3b and 3c are disposed at places positioned at peaks of a triangular shape formed in a circular cross-section perpendicular to the longitudinal axis of the longitudinal member 3.

The proximal end of the open-close manipulation wire 30 is connected to the open-close manipulation member 130. The proximal ends of the advance-retreat manipulation wires 31 and 32 are connected to the first advance-retreat manipulation member 131 and the second advance-retreat manipulation member 132, respectively.

Accordingly, an operator can open and close the jaws 11 and 12 via the manipulation wire 30 through a slide manipulation of the open-close manipulation member 130. In addition, the operator can independently advance and retreat the loop wire 23 of the grasping members 21 and 22 and expand and contract the loop wire 23 via the manipulation wires 31 and 32 through a slide manipulation of the first advance-retreat manipulation member 131 and the second advance-retreat manipulation member 132.

An action of the endoscopic device 1A according to the embodiment will be described as an example of a procedure using the endoscopic device 1A.

Figure 11:
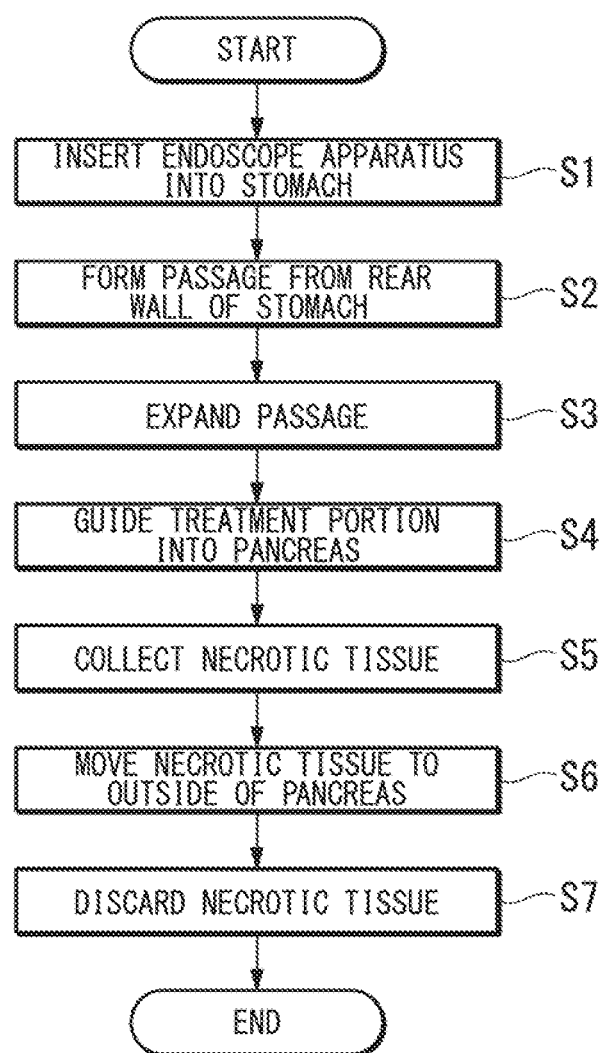
FIG. 11 is a flowchart showing a process of an example of a procedure using the endoscopic device according to the first embodiment of the present invention.

FIG. 11 is a flowchart showing a process of the procedure using the endoscopic device 1A according to the embodiment. FIGS. 12 to 19 are views showing a process of the procedure.

The procedure exemplified in the embodiment is a procedure referred to as a pancreatic necrosectomy. A pancreatic necrosectomy is a procedure of removing necrotic pancreatic tissue from the pancreas by taking the tissue into the alimentary canal or to the outside of the body. In order to perform the procedure, the endoscope apparatus 500, an endoscope puncture needle 510, an endoscope expansion catheter 520, and the endoscopic device 1A according to the embodiment are used.

Before starting the procedure, the endoscopic device 1A is held in a state in which the jaws 11 and 12 are closed. In addition, the grasping members 21 and 22 are reduced to a minimum size. When the loop wire 23 that constitutes the grasping members 21 and 22 can be received in the jaws 11 and 12, the loop wire 23 is received in the jaws 11 and 12. That is, before starting the procedure, the manipulation members 130, 131 and 132 shown in FIG. 6 are pulled toward the proximal end side.

Figure 12:
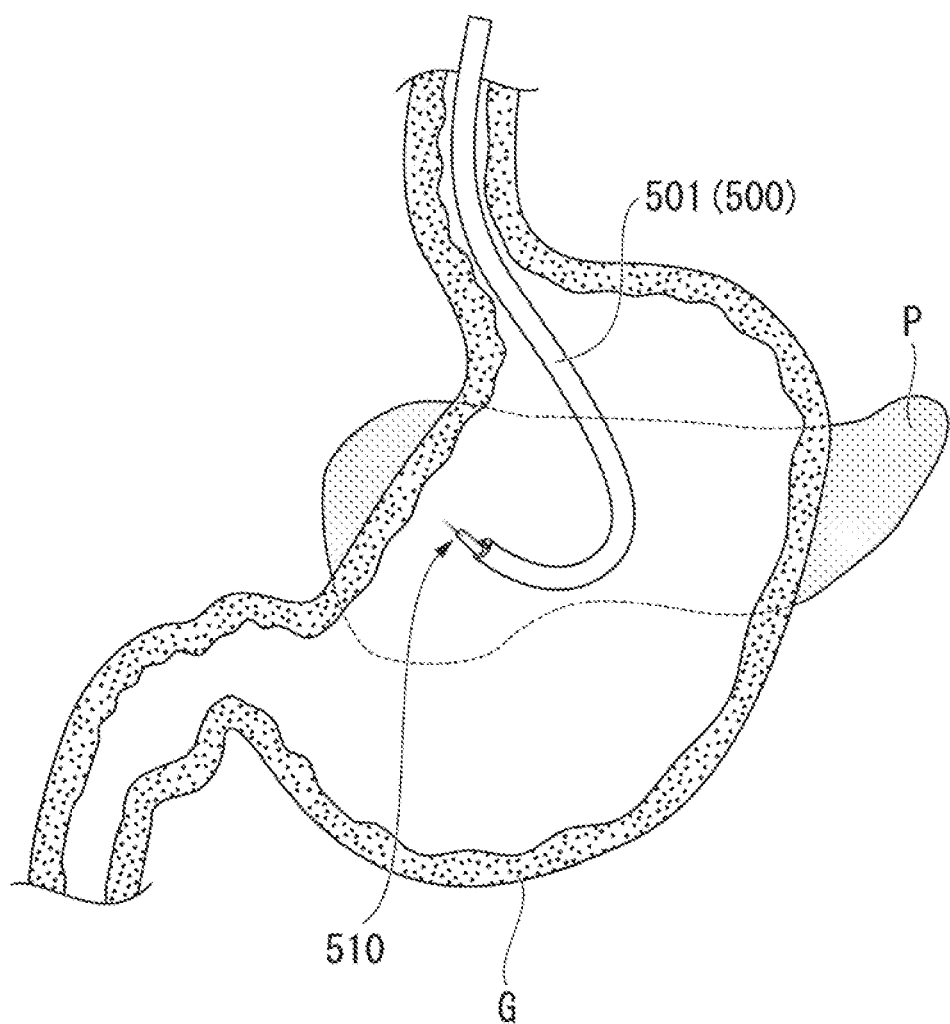
FIG. 12 is a view showing a process of the procedure using the endoscopic device according to the first embodiment of the present invention.
Figure 13:
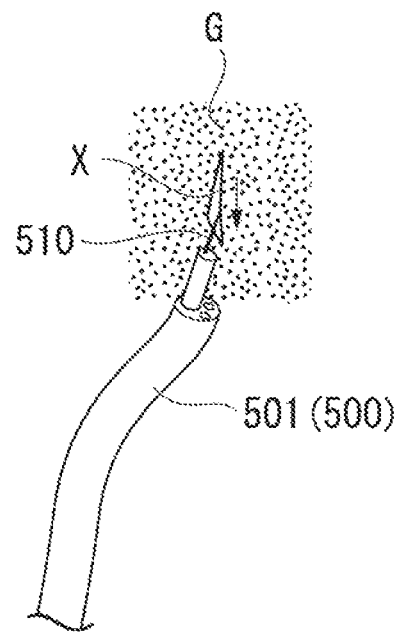
FIG. 13 is a view showing the process of the procedure using the endoscopic device according to the first embodiment of the present invention.

First, the insertion portion 501 of the endoscope apparatus 500 is inserted into the stomach of a patient (step S1 shown in FIG. 11). In step S1, as shown in FIG. 12, the distal end of the insertion portion 501 of the endoscope apparatus 500 passes through the esophagus from the mouth to be disposed in the stomach G. In step S1, as the operator observes the inside of the stomach using an endoscope image, an area appropriate for incision is selected. Here, step S1 is terminated, and step S2 is performed.

Step S2 is a step of incising a rear wall of the stomach and forming a passage configured to guide the endoscopic device 1A into the pancreas at the stomach and the pancreas. In step S2, in order to incise the area selected in step S1, the above-mentioned endoscope puncture needle 510 is attached to the endoscopic device channel 502 of the endoscope apparatus 500. The operator opens a hole at the rear wall of the stomach using an endoscope high frequency knife 510, and forms an opening portion X (see FIG. 13). Here, step S2 is terminated, and step S3 is performed.

Step S3 is a step of expanding the passage (the opening portion X) formed in the step S2. In step S3, a guide wire is introduced into the body through an inner tube (not shown) formed in the endoscope high frequency knife 510. Further, the endoscope expansion catheter 520 is introduced into the body along the guide wire. The distal end of the endoscope expansion catheter 520 is guided to the opening portion X formed in the stomach by the guide wire. As the endoscope expansion catheter 520 is guided to the opening portion X, a balloon portion of the endoscope expansion catheter 520 is inserted into the opening portion X formed in step S2.

Figure 14:
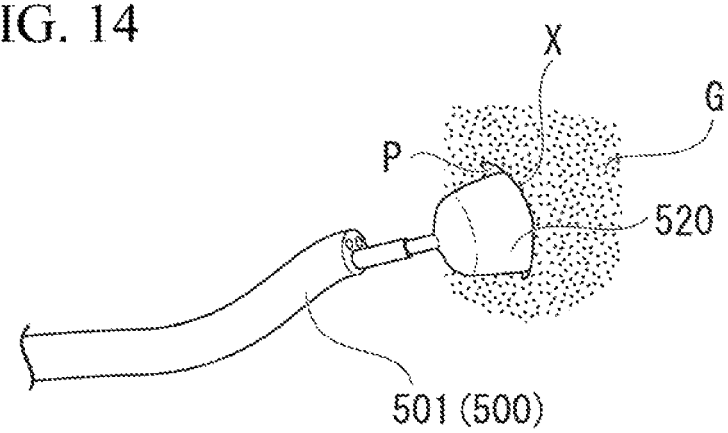
FIG. 14 is a view showing the process of the procedure using the endoscopic device according to the first embodiment of the present invention.

After that, the balloon portion is expanded to expand the opening portion X to a desired size as shown in FIG. 14. Accordingly, in step S3, the passage expanded to a size such that the treatment portion 10 can be inserted into the pancreas from the inside of the stomach is formed at the stomach and the pancreas.

When the opening portion X is further expanded, for example, a high frequency endoscopic device configured to incise the tissue using high frequency current is used.

As the opening portion X of the desired size is formed, the endoscope expansion catheter 520 is removed. Here, step S3 is terminated, and step S4 is performed.

Step S4 is a step of guiding the treatment portion 10 into the pancreas through the passage expanded in step S3.

In step S4, the endoscopic device 1A is attached to the endoscope channel 502 of the endoscope apparatus 500 (see FIG. 1). In addition, the endoscope puncture needle or the endoscope expansion catheter may be removed from the endoscope channel, and the endoscopic device 1A may be attached to the endoscope channel using the guide wire that becomes usable thereby.

The treatment portion 10 and the insertion portion 2 are inserted into the endoscope channel 502. Then, the distal end of the longitudinal member 3 of the endoscopic device 1A protrudes from the distal end of the endoscope channel 502.

Figure 15:
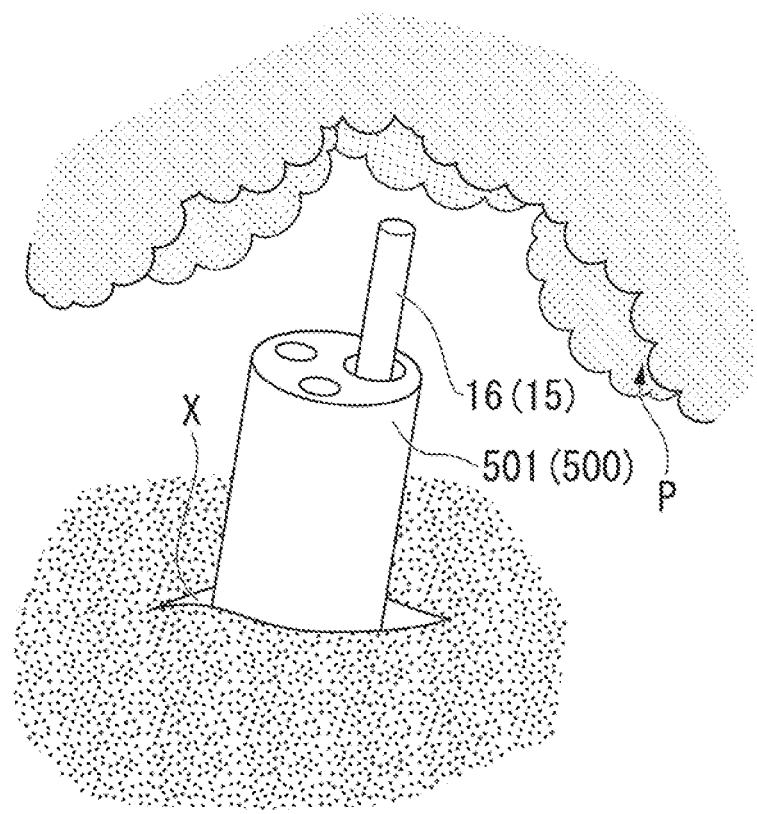
FIG. 15 is a view showing the process of the procedure using the endoscopic device according to the first embodiment of the present invention.

After that, the operator who manipulates the endoscope apparatus 500 to which the endoscopic device 1A is attached guides the distal end of the longitudinal member 3 into the pancreas through the inside of the opening portion X formed at the stomach and the pancreas through a curve manipulation or by moving the insertion portion 501 of the endoscope apparatus 500 (see FIG. 15). As the endoscopic device 1A enters the pancreas, the guide wire is removed. Here, step S4 is terminated, and step S5 is performed.

Step S5 is a step of collecting the necrotic tissue using the treatment portion 10 guided into the pancreas in step S4.

In step S5, the operator observes the image obtained by the endoscope apparatus 500 and adjusts the position of the treatment portion 10. Next, the operator moves the distal end of the endoscope apparatus 500 toward a tissue P in which the necrotic tissue is present as a collecting target.

Figure 16:
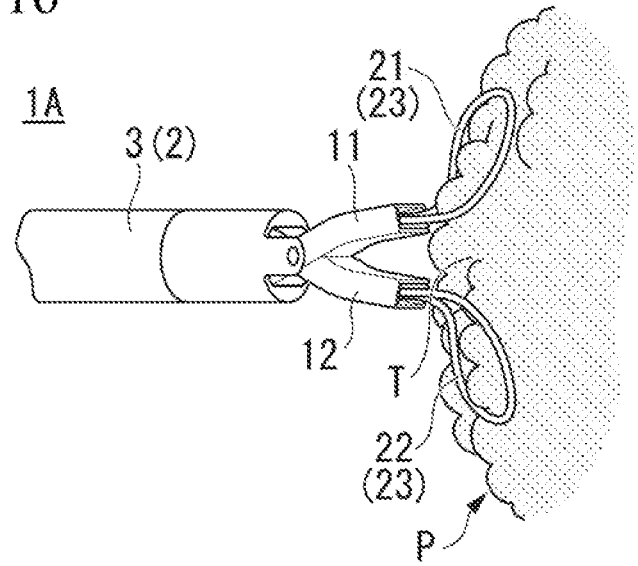
FIG. 16 is a view showing the process of the procedure using the endoscopic device according to the first embodiment of the present invention.
Figure 17:
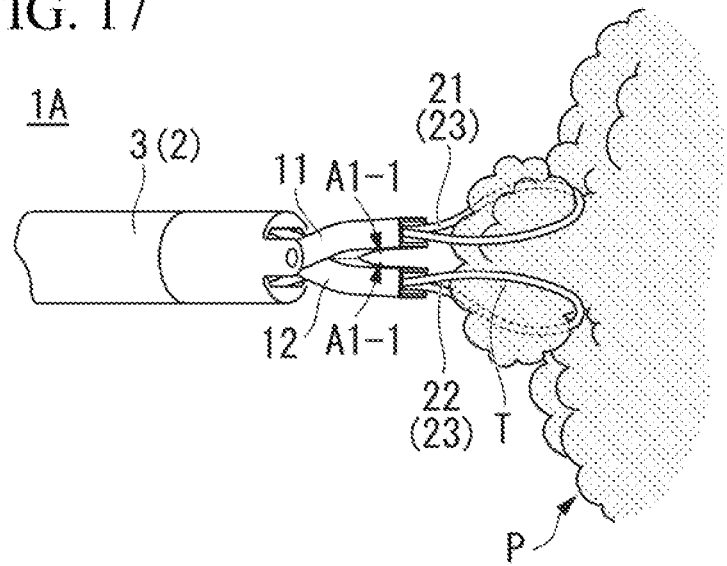
FIG. 17 is a view showing the process of the procedure using the endoscopic device according to the first embodiment of the present invention.

As shown in FIG. 16, as front surfaces of the distal ends of the jaws 11 and 12 arrive at a position corresponding to the necrotic tissue T, the open-close manipulation member 130 and the advance-retreat manipulation members 131 and 132 are moved to the distal end side. As a result, the pair of jaws 11 and 12 are opened, and the pair of grasping members 21 and 22 are widened. Next, the operator closes the pair of jaws 11 and 12 as shown in FIG. 17 while pressing the curved portions of the distal ends of the loop wires 23 of the grasping members 21 and 22 against the tissue P. Further, the pair of jaws 11 and 12 may be completely closed or may not be completely closed. That is, the jaws 11 and 12 may be moved such that the loop wire 23 installed at the first jaw 11 and the loop wire 23 installed at the second jaw 12 approach each other.

As the jaws 11 and 12 are closed, the necrotic tissue T is sandwiched by the loop wires 23 of the grasping members 21 and 22.

Figure 18:
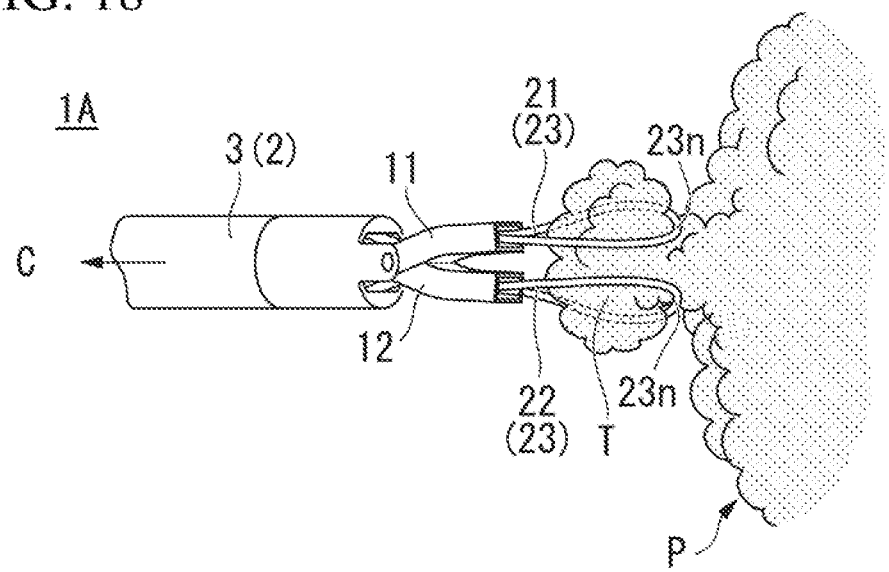
FIG. 18 is a view showing the process of the procedure using the endoscopic device according to the first embodiment of the present invention.
Figure 19:
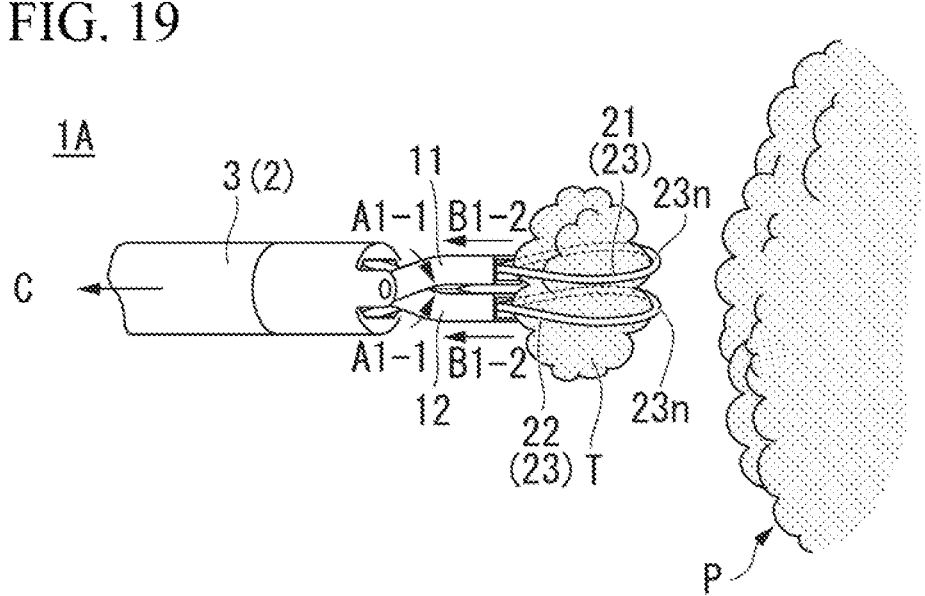
FIG. 19 is a view showing the process of the procedure using the endoscopic device according to the first embodiment of the present invention.

Next, as shown in FIG. 18, when the necrotic tissue T is sandwiched, the operator pulls the insertion portion 2 in an arrow C direction. In addition, as shown in FIG. 19, the operator closes the pair of jaws 11 and 12 by pulling the insertion portion 2 in the arrow C direction and closes the pair of grasping members 21 and 22. Then, the necrotic tissue T is caught in the loop wires 23 of the pair of grasping members 21 and 22 and separated from the tissue P. Further, even when the incision or the like for separating the necrotic tissue T from the normal tissue is not performed, if the insertion portion 2 is pulled in the arrow C direction, the necrotic tissue T in the pancreas is caught in the loop wire 23 and separated from the normal tissue P. The necrotic tissue T grasped by the pair of grasping members 21 and 22 is collected by the endoscopic device 1A while being sandwiched between the pair of grasping members 21 and 22.

In the endoscopic device 1A according to the embodiment, the pair of grasping members 21 and 22 configured to be opened and closed in a direction crossing the longitudinal axis of the longitudinal member 3 include the loop wire 23 curved in an annular shape within a plane crossing the open-close direction of the jaws 11 and 12. Accordingly, by pinching a large amount of the necrotic tissue T by the loop wires 23 in a state that the loop wires 23 of the pair of grasping members s 21 and 22 are opened, a portion of the necrotic tissue T can be captured in the loop of the loop wire 23 with the pinching force. That is, as the grasping force is applied from the loop wire 23 to the necrotic tissue T, the necrotic tissue T is pushed into the loop. For this reason, when the longitudinal member 3 is pulled toward the operator in a state in which the necrotic tissue T is inside the loop, a wire portion of a distal point 23n of the loop wire 23 separated farthest from the jaws 11 and 12 and the necrotic tissue T cross with respect to a direction of pulling the necrotic tissue T. Accordingly, the necrotic tissue T can be easily caught and entwined by the loop wire 23. In this way, in the embodiment, as the necrotic tissue T is entwined by the loop wire 23, the large amount of the necrotic tissue T can be removed with one manipulation in comparison with the case in which the necrotic tissue T is removed using a general forceps.

In addition, upon collection of the necrotic tissue T, as shown in FIG. 19, the operator pulls the advance-retreat manipulation wires 31 and 32 to move the wires in arrow B1-2 and B2-2 directions. In this way, the size of the loops of the loop wires 23 of the grasping members 21 and 22 is reduced, and the necrotic tissue T is securely held by the loop wires 23. In addition, since the size of the loop wires 23 can be previously adjusted to correspond to the size of the necrotic tissue T serving as a removing target, the loop wire 23 can be easily set to an appropriate loop diameter such that the necrotic tissue T can be effectively removed. Here, step S5 is terminated, and step S6 is performed.

Step S6 is a step of moving the necrotic tissue collected in step S5 to the outside of the pancreas.

The operator returns the treatment portion 10 into the stomach from the inside of the pancreas by moving the insertion portion 501 of the endoscope apparatus 500 or moving the longitudinal member 3 with respect to the endoscope channel 502 in a state in which the jaws 11 and 12 are closed. Here, step S6 is terminated, and step S7 is performed.

Step S7 is a step of discarding the necrotic tissue in the stomach.

In step S7, first, the operator opens the jaws 11 and 12. In addition, the operator enlarges the loops of the loop wires 23 of the grasping members 21 and 22. As a result, the necrotic tissue T grasped by the loop wires 23 of the grasping members 21 and 22 is separated from the loop wire 23 to be thrown away in the stomach.

Here, when the necrotic tissue T is caught in or attached to the loop wire 23 and is not easily removed, the operator individually enlarges or reduces the loop wires 23 of the first grasping member 21 and the second grasping member 22. Accordingly, removal of the necrotic tissue T is promoted.

The necrotic tissue T thrown away in the stomach is excreted through the alimentary canal. In addition, in step S7, the treatment portion 10 in which the necrotic tissue is accommodated may be discharged to the outside of the body according to necessity. In this case, the entire endoscopic device 1A may be discharged to the outside of the body with the endoscope apparatus 500. In addition, when the treatment portion 10 has a size that is retracted into the endoscope channel 502 in a state in which the necrotic tissue T is held, the treatment portion 10 in which the necrotic tissue T is accommodated may be drawn to the outside of the body through the endoscope channel 502. The necrotic tissue drawn to the outside of the body may be used for pathologic examination. Here, step S7 is terminated.

In the procedure, when the amount of the necrotic tissue required to be scraped out of the pancreas is very large, steps from step S4 to step S7 can be repeated a plurality of times.

In the endoscopic device 1A according to the embodiment, the pair of grasping members 21 and 22 are installed at the jaws 11 and 12 to be opened and closed in the direction crossing the longitudinal axis of the longitudinal member 3. Accordingly, the grasping members 21 and 22 can be freely opened and closed with respect to the size of the tissue to be removed. In a state in which the jaws 11 and 12 are largely opened, much tissue can be collected when the loop wire 23 is closed with the jaws 11 and 12 in the next step.

In the endoscopic device of the related art, when the tissue is grasped by the grasping members having a small grasping area, a small amount of the tissue may be torn off. However, like in the embodiment, when the grasping members 21 and 22 are constituted by the loop wires 23 curved in an annular shape, since a substantial grasping surface is largely widened, a large range of tissue is collected. In addition, as the tissue is grasped at a substantially large area, since the grasping force is distributed, a large amount of the tissue is collected without breaking off.

In the endoscopic device 1A according to the embodiment, the grasping members 21 and 22 include the loop wire 23 bent in an annular shape within a plane crossing the open-close direction of the jaws 11 and 12. Accordingly, as the large amount of necrotic tissue T is pinched in a state in which the loop wires 23 of the pair of grasping members 21 and 22 are opened, some of the necrotic tissue T can be captured at the inside of the loops of the loop wires 23 with the pinching force. That is, as the grasping force is applied from the loop wires 23 to the necrotic tissue T, the necrotic tissue T is pressed into the loop. For this reason, in this state, as the operator pulls the longitudinal member 3 toward the operator's body, the necrotic tissue T can be caught in the loop wire 23 to be securely collected.

In the endoscopic device 1A according to the embodiment, since the grasping members 21 and 22 are constituted by the loop wires 23 having flexibility, the grasping force can be smoothly applied to the tissue, and the necrotic tissue can be smoothly collected without applying an excessive force. Since the loop wire 23 has a shape closed in a loop shape, the loop wire 23 is not needlessly deformed with a reaction force received from the tissue. In addition, as the grasping members 21 and 22 are constituted by the loop wires 23, since the portion abutting the tissue becomes a curved wire portion, damage to the tissue such as bleeding or the like can be prevented.

In the endoscopic device 1A according to the embodiment, since the first grasping member 21 and the second grasping member 22 are configured to be freely enlarged or reduced, the substantial grasping area of the first grasping member 21 and the second grasping member 22 can be varied. Accordingly, the size of the treatment portion 10 of the endoscopic device 1A can be varied according to the size of the necrotic tissue of the collecting target. Since the loop wires 23 that constitute the grasping members 21 and 22 are installed to freely advance and retreat with respect to the jaws 11 and 12, the loop wire 23 can be contracted to be small upon insertion into the human body, and opened to be large upon collection of the tissue.

In particular, in the endoscopic device 1A according to the embodiment, the loop wires 23 of the grasping members 21 and 22 can independently advance and retreat and be enlarged or reduced, and the collected tissue can be easily removed from the grasping members 21 and 22. For example, the endoscopic device 1A can contract the loop wire 23 of the second grasping member in a state in which the loop wire 23 of the first grasping member 21 is widened, or can be manipulated in a reverse manner. Accordingly, according to the endoscopic device 1A of the embodiment, as the above-mentioned enlarging or reducing operation is repeated at each of the grasping members 21 and 22, even when the collected tissue is caught in the wire, the collected tissue can be easily removed.

In the embodiment, the case in which the loop wire 23 of the first grasping member 21 and the loop wire 23 of the second grasping member 22 are configured to individually advance and retreat and be freely enlarged or reduced is shown. However, the loop wires 23 of both of the grasping members 21 and 22 may be configured to advance and retreat and be freely enlarged or reduced simultaneously and integrally rather than individually. In this case, the advance-retreat manipulation wires 31 and 32 are integrated as one wire.

In addition, even when the loop wires 23 of the grasping members 21 and 22 are not configured to freely advance and retract and be enlarged or reduced, if the loop wires 23 are configured to be freely opened and closed, the endoscopic device 1A can obtain a good collecting effect.

First Modified Example of First Embodiment

Figure 20:
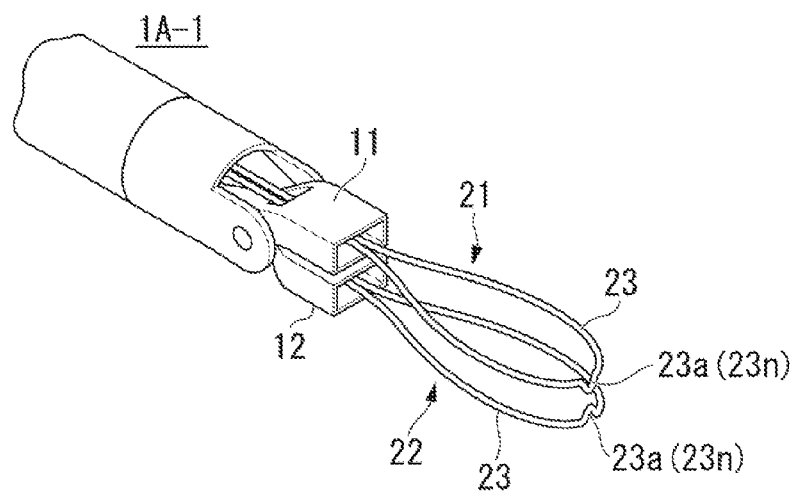
FIG. 20 is a perspective view showing a configuration of a first modified example of the first embodiment of the present invention.
Figure 21:
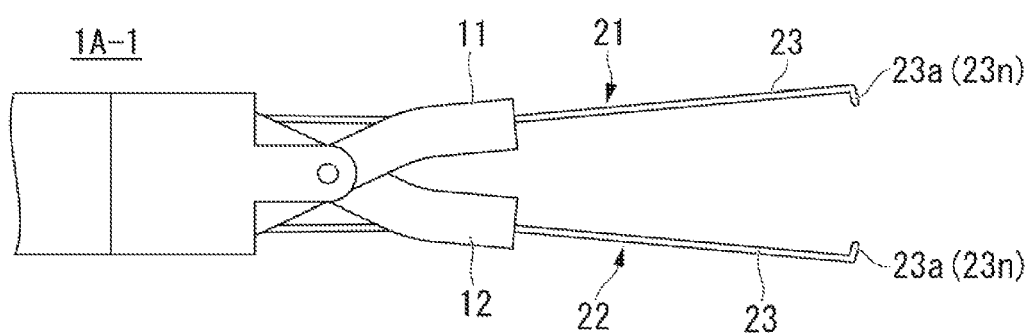
FIG. 21 is a side view showing the configuration of the first modified example of the first embodiment of the present invention.

Next, a first modified example of the embodiment will be described. FIG. 20 is a perspective view showing a configuration of an endoscopic device 1A-1 of the first modified example. FIG. 21 is a side view showing the configuration of the endoscopic device 1A-1 of the first modified example.

As shown in FIGS. 20 and 21, in the modified example, a convex portion 23a is formed at the distal end of the loop wire 23 that constitutes each of the grasping members 21 and 22. The distal end of the loop wire 23 is the distal point 23n maximally spaced apart from the jaws 11 and 12. The convex portion 23a is formed to protrude at a grasping side with respect to the object to be grasped, i.e., a side opposite to the pair of grasping members 21 and 22. In this way, as the convex portion 23a is formed at the distal end of the loop wire 23, the collecting target tissue is likely to be hooked by the convex portion 23a.

Second Modified Example of First Embodiment

Figure 22:
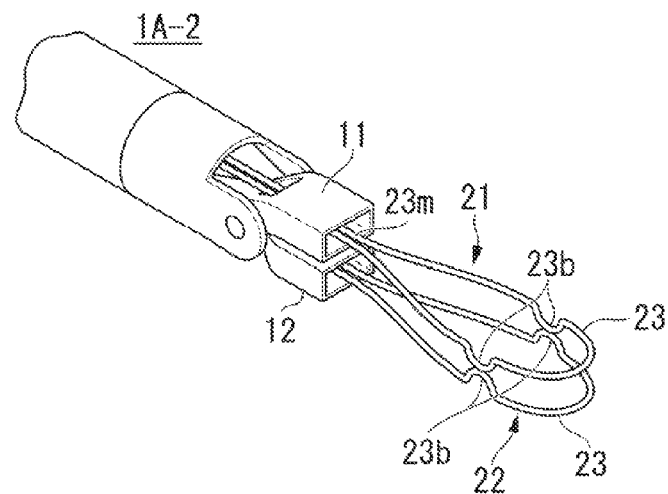
FIG. 22 is a perspective view showing a configuration of a second modified example of the first embodiment of the present invention.
Figure 23:
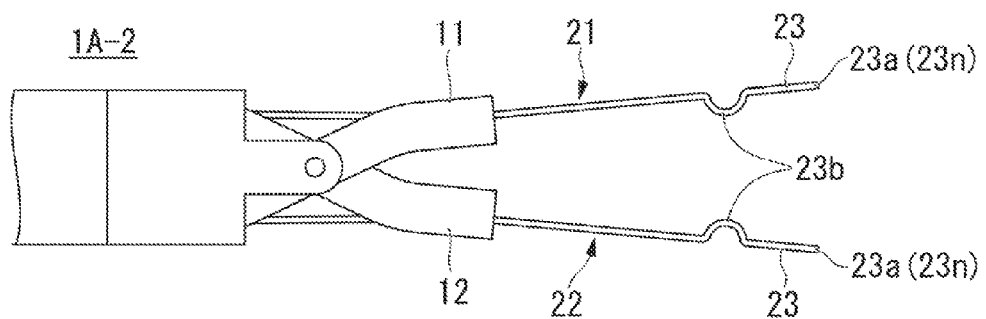
FIG. 23 is a side view showing the configuration of the second modified example of the first embodiment of the present invention.

Next, a second modified example of the embodiment will be described. FIG. 22 is a perspective view showing a configuration of an endoscopic device 1A-2 of the second modified example. FIG. 23 is a side view showing the configuration of the endoscopic device 1A-2 of the second modified example.

As shown in FIGS. 22 and 23, in the modified example, convex portions 23b are formed at the middle between the distal end and the proximal end of the loop wire 23 that constitutes each of the grasping members 21 and 22. The proximal end of the loop wire 23 is a proximal point 23m closest to the jaws 11 and 12. Accordingly, the middle between the distal end and the proximal end of the loop wire 23 is the middle between the distal point 23n and the proximal point 23m of the loop wire 23. In addition, the convex portion 23b is formed to protrude in a wave form at a grasp side with respect to the object to be grasped, i.e., a side opposite to the pair of grasping members 21 and 22, when seen from a side view. In this way, as the convex portion 23b is formed at the distal end of the loop wire 23, the collected tissue is likely to be hooked by the convex portion 23b. The convex portions 23b may be disposed at deviated positions, in addition to the case in which they are formed at the same position of the first grasping member 21 and the second grasping member 22.

Third Modified Example of First Embodiment

Figure 24:
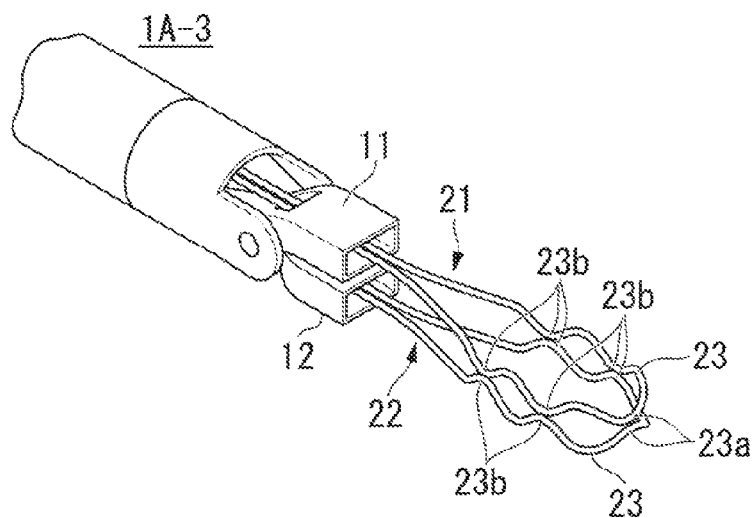
FIG. 24 is a perspective view showing a configuration of a third modified example of the first embodiment of the present invention.
Figure 25:
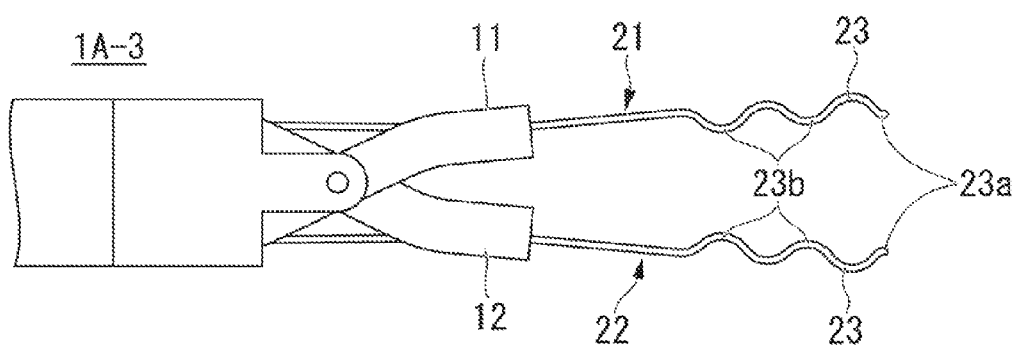
FIG. 25 is a side view showing the configuration of the third modified example of the first embodiment of the present invention.

Next, a third modified example of the embodiment will be described. FIG. 24 is a perspective view showing a configuration of an endoscopic device 1A-3 of the third modified example. FIG. 25 is a side view showing a configuration of the endoscopic device 1A-3 of the third modified example.

As shown in FIGS. 24 and 25, in the modified example, a plurality of convex portions 23a and 23b are formed at the distal end of the loop wire 23 that constitutes each of the grasping members 21 and 22, and the middle between the distal end and the proximal end of the loop wire 23. That is, the modified example corresponds to the case in which the first modified example and the second modified example are combined, and further, the plurality of convex portions 23b of the second modified example are formed. In this way, as the plurality of convex portions 23a and 23b are formed, and the collected tissue is more likely to be hooked by the convex portions 23a and 23b. The convex portions 23b may be disposed at deviated positions, in addition to the case in which they are formed at the same position of the first grasping member 21 and the second grasping member 22.

Fourth Modified Example of First Embodiment

Figure 26:
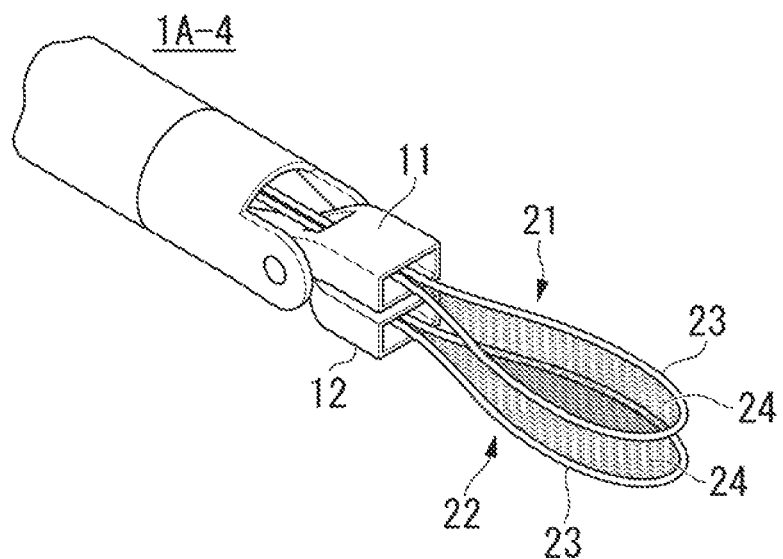
FIG. 26 is a perspective view showing a configuration of a fourth modified example of the first embodiment of the present invention.

Next, a fourth modified example of the embodiment will be described. FIG. 26 is a perspective view showing a configuration of an endoscopic device 1A-4 of the fourth modified example.

As shown in FIG. 26, in the modified example, a net 24 stretched on a surface surrounding the loop wire 23 is installed at the loop wires 23 that constitute each of the grasping members 21 and 22.

As a material of the net 24, a thread-like material that can be used in the body such as a suture or the like used for surgery, specifically, a thread formed of a resin such as nylon, rubber, or the like, silk, or cotton can be employed. In addition, the net 24 may be formed of a metal wire having biocompatibility generally used for the endoscopic device, specifically, a single wire or a stranded wire formed of stainless steel or a super-elastic alloy (NiTi alloy or the like). A size of a mesh of the net 24 may be appropriately set according to the state of the treatment target area. In this way, as the net 24 is stretched by the loop wire 23, dropping of the collected tissue is prevented.

In the modified example, while the case in which the nets 24 are stretched by the loop wires 23 of both of the grasping members 21 and 22 is shown, the net 24 may be stretched by the loop wire 23 of any one of the grasping members.

Fifth Modified Example of Fifth Embodiment

Figure 27:
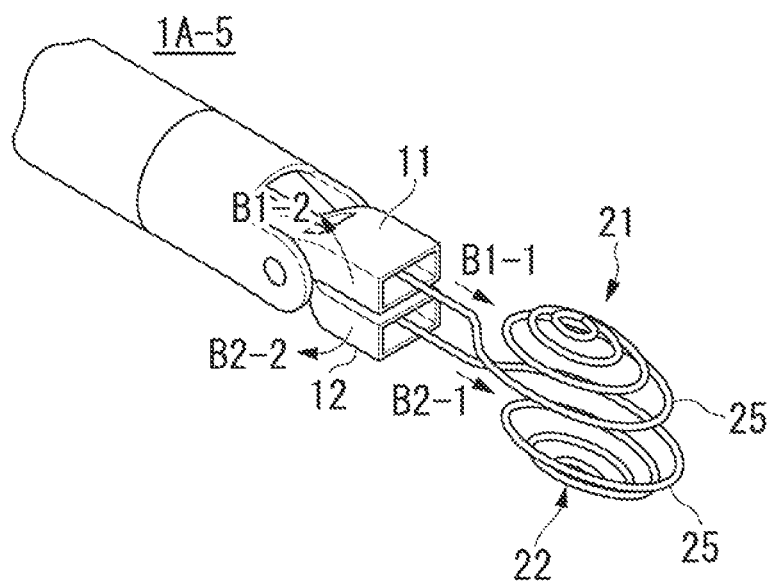
FIG. 27 is a perspective view showing a configuration of a fifth modified example of the first embodiment of the present invention.

Next, a fifth modified example of the embodiment will be described. FIG. 27 is a perspective view showing a configuration of the fifth modified example.

As shown in FIG. 27, in the modified example, the pair of grasping members 21 and 22 are constituted by wires 25 curved in a spiral shape. A spiral of the wire 25 may be formed in a two-dimensional shape, or may be formed in a three-dimensional shape having swelling in a direction perpendicular to the open-close direction of the grasping members 21 and 22.

As the wires 25 curved in a spiral shape are formed of a shape memory alloy, the wires 25 are formed in a spiral shape while protruding from the jaws 11 and 12. The wires 25 are installed to advance and retreat with respect to the jaws 11 and 12.

For example, as the wires 25 are pushed in arrow B1-1 and B2-1 directions shown in FIG. 27, the wires 25 are deformed in a spiral shape with expansion. In addition, as the wires 25 are drawn in the arrow B1-2 and B2-2 directions shown in FIG. 27, the wires 25 are received in the jaws 11 and 12. Even in this case, the wire 25 of the first grasping member 21 and the wire 25 of the second grasping member 22 are installed to advance and retreat individually.

In this way, in the modified example, as the grasping members 21 and 22 are constituted by the spiral wires 25, like in the fourth modified example, an effect similar to the case in which the collected tissue is held by the net 24 not to be dropped is exhibited. In addition, the spiral wire 25 can come in contact with the tissue with a small force more softly than that of the loop wire 23.

In the modified example, the case in which both of the pair of grasping members 21 and 22 are constituted by the spiral wires is shown. However, only one of the grasping members may be constituted by the spiral wire, and the other grasping member may be constituted by, for example, the above-mentioned loop wire 23 shown in FIG. 2.

Sixth Modified Example of First Embodiment

Next, a sixth modified example of the embodiment will be described.

In the modified example, a ratchet (not shown) configured to move the open-close manipulation wire 30 at a certain pitch is installed at the operating portion 100. The ratchet of the modified example is a ratchet configured with a pitch defined by engaging protrusions, like a ratchet installed at a Pean forceps. The pitch defined in the ratchet is set such that, for example, a degree of open-close of the pair of jaws is switched 3 to 5 steps between a complete closing state and a complete opening state of the pair of jaws 11 and 12. Accordingly, in the modified example, the position of the open-close manipulation wire 30 can be fixed with respect to the operating portion 100 using the ratchet. As a result, according to the endoscopic device 1A of the modified example, an opening angle of the pair of jaws 11 and 12 can be finely adjusted or the positions of the jaws 11 and 12 can be fixed.

In addition, according to the endoscopic device 1A of the modified example, a grasping capability can be easily adjusted according to hardness, viscosity, or the like, of the tissue serving as a grasping target.

The ratchet according to the same principle as the modified example may be installed at the operating portion 100 in order to move the advance-retreat manipulation wires 31 and 32 at a certain pitch. In this case, the size of the loop is finely adjusted by the loop wire 23, and the loop can be easily maintained at the finely adjusted size.

Second Embodiment

Next, an endoscopic device 1B of a second embodiment of the present invention will be described. Further, in the embodiments to be described below, the same components as in the above-mentioned first embodiment are designated by the same reference numerals, and overlapping descriptions will be omitted here.

Figure 28:
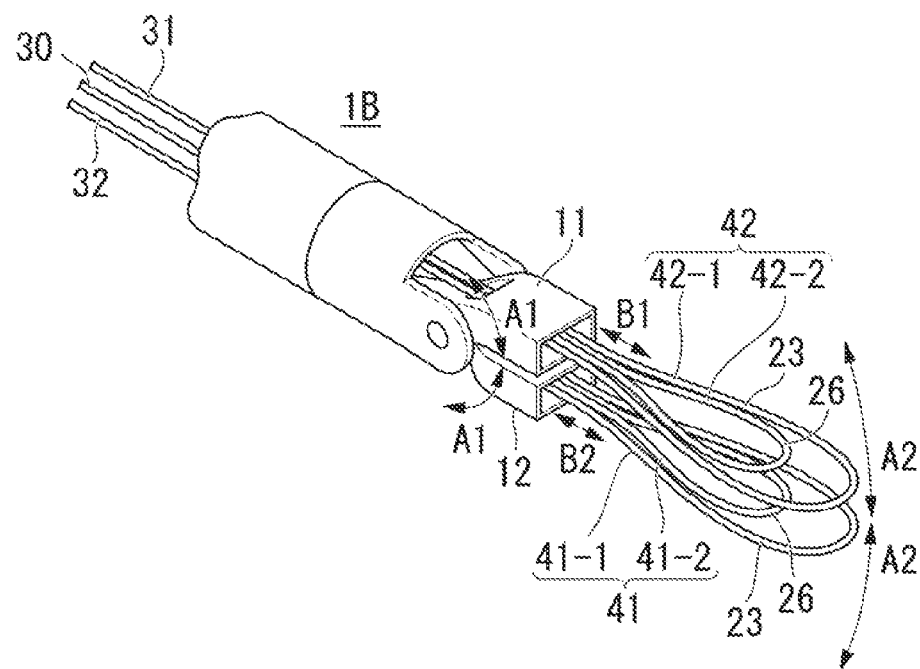
FIG. 28 is a view showing a configuration of a treatment portion of a distal end of an endoscopic device of a second embodiment of the present invention.

FIG. 28 is a view showing a configuration of a treatment portion of the distal end of the endoscopic device of the second embodiment of the present invention. As shown in FIG. 28, in a treatment portion 40 of the endoscopic device 1B, a first grasping member 41 and a second grasping member 42 are constituted by a set of a plurality of grasping members which are positioned at an outward of the grasping members and an inward of the grasping members, respectively.

The grasping members positioned at the outward thereof are main grasping members 411 and 421. The grasping members positioned at the inward of the grasping members are auxiliary grasping members 412 and 422. The main grasping members 411 and 421 positioned at the outward of the grasping members correspond to the grasping members 21 and 22 of the first embodiment. The auxiliary grasping members 412 and 422 positioned at the inward of the grasping members in an expanded state are formed to be smaller than the main grasping members 411 and 421 positioned at the outward of the grasping members.

The main grasping members 411 and 421 positioned at the outward of the grasping members and the auxiliary grasping members 412 and 422 positioned at the inward of the grasping members are also constituted by the loop wires 23 and 26 curved in a loop shape. A size of a loop of an auxiliary loop wire (an auxiliary wire) 26 is formed to be smaller than that of a loop of a main loop wire (a main wire) 23. The auxiliary loop wire 26 is disposed to have an interval inside the main loop wire 23 positioned at the outward of the grasping members.

The main loop wire 23 and the auxiliary loop wire 26 are connected to the distal ends of the advance-retreat manipulation wires 31 and 32 by joining the starting ends and the terminating ends of the wires 23 and 26. Accordingly, the main loop wire 23 and the auxiliary loop wire 26 advance and retreat with an advance-retreat manipulation of the advance-retreat manipulation wires 31 and 32 to enlarge or reduce the size of the loop.

In this way, in the endoscopic device 1B according to the embodiment, since each of the first grasping member 41 and the second grasping member 42 is constituted by a set of the main loop wire 23 and the auxiliary loop wire 26, when the tissue is collected, a tangled portion of the grasping members 41 and 42 and the tissue is increased. According to the embodiment, the tissue can be more securely collected. In addition, according to the embodiment, the collected tissue held once is hard to lose. The other effects are the same as those of the first embodiment.

A configuration in which only the auxiliary loop wire 26 cannot freely advance and retreat and cannot be freely enlarged or reduced may be provided. Alternatively, a configuration in which only the main loop wire 23 cannot freely advance and retreat and cannot be freely enlarged or reduced may be provided.

In addition, in the second embodiment, while the case in which each of the pair of grasping members 41 and 42 is constituted by the main grasping members 411 and 421 and the auxiliary grasping members 412 and 422 is shown, the number of auxiliary grasping members may be set to 2 or more. In addition, any one of the grasping members 41 and 42 may be constituted by only the main grasping member without the auxiliary grasping member.

First Modified Example of Second Embodiment

Figure 29:
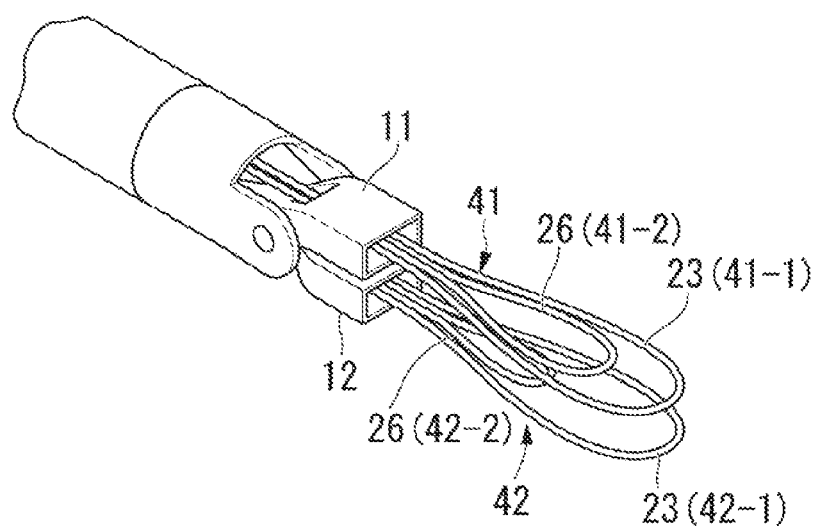
FIG. 29 is a perspective view schematically showing a first modified example of the second embodiment of the present invention.

Next, a first modified example of the embodiment will be described. FIG. 29 is a perspective view showing a configuration of the first modified example.

As shown in FIG. 29, in the modified example, in the pair of grasping members 41 and 42 supported by the jaws 11 and 12, the size of the loop of the auxiliary loop wire 26 of one grasping member 41 is different from the size of the loop of the auxiliary loop wire 26 of the other grasping member 42. In this case, the size of the loop of the auxiliary loop wire 26 is not varied. In this way, when the size of the loop of the auxiliary loop wire 26 is different at the one grasping member 41 and the other grasping member 42, the large side and the small side of the loop can be discriminated according to the size of the collected tissue.

Next, the second modified example to the fifth modified example of the embodiment will be described using FIGS. 30 to 33. Further, in FIGS. 30 to 33, while a schematic configuration of only one grasping member of the first grasping member 41 and the second grasping member 42 supported by the jaws 11 and 12 is shown, the other grasping member also has the same configuration. Alternatively, a combination of the other grasping member is not particularly limited as long as only the main loop wire 23 or the main loop wire 23 and the auxiliary loop wire 26 are provided.

Second Modified Example of Second Embodiment

Figure 30:
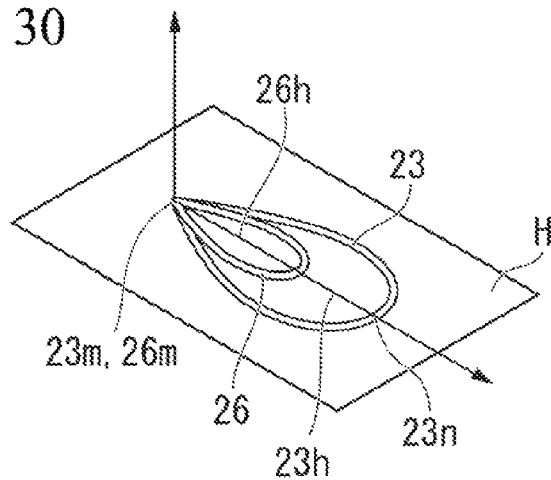
FIG. 30 is a perspective view schematically showing a grasping member of a second modified example of the second embodiment of the present invention.

FIG. 30 is a perspective view schematically showing a grasping member of a second modified example of the second embodiment.

As shown in FIG. 30, in the modified example, a straight line connecting the proximal point 23*m* supported by a jaw of the main loop wire 23 and the distal point 23*n* maximally spaced apart from the jaw is defined as a centerline 23*h* of the main loop wire 23. In addition, a straight line connecting a proximal point 26*m* supported by a jaw of the auxiliary loop wire 26 and a distal point 26*n* maximally spaced apart from the jaw is defined as a centerline 26*h* of the auxiliary loop wire 26.

In the modified example, the centerline 23*h* of the main loop wire 23 and the centerline 26*h* of the auxiliary loop wire 26 overlap in the same plane H including both of the main loop wire 23 and the auxiliary loop wire 26.

Third Modified Example of Second Embodiment

Figure 31:
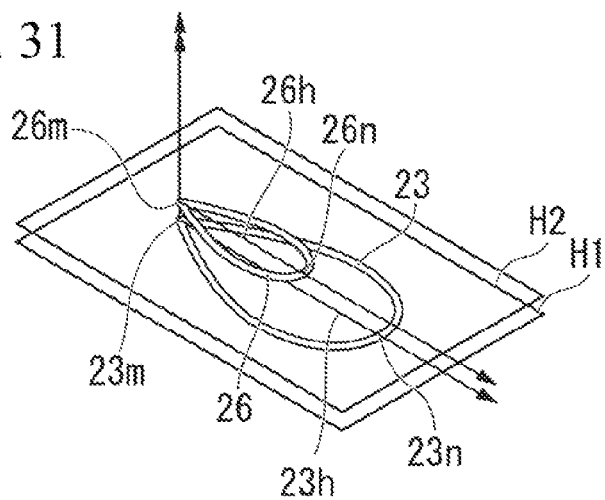
FIG. 31 is a perspective view schematically showing a grasping member of a third modified example of the second embodiment of the present invention.

FIG. 31 is a perspective view schematically showing one grasping member of a third modified example of the second embodiment.

As shown in FIG. 31, in the modified example, the plane H1 including the main loop wire 23 and the plane H2 including the auxiliary loop wire 26 have a relation in which they are parallel to each other with an interval therebetween.

In the modified example, the centerline 23h of the main loop wire 23 and the centerline 26h of the auxiliary loop wire 26 are formed at a position overlapping when seen in a direction perpendicular to both of the planes H1 and H2.

Fourth Modified Example of Second Embodiment

Figure 32:
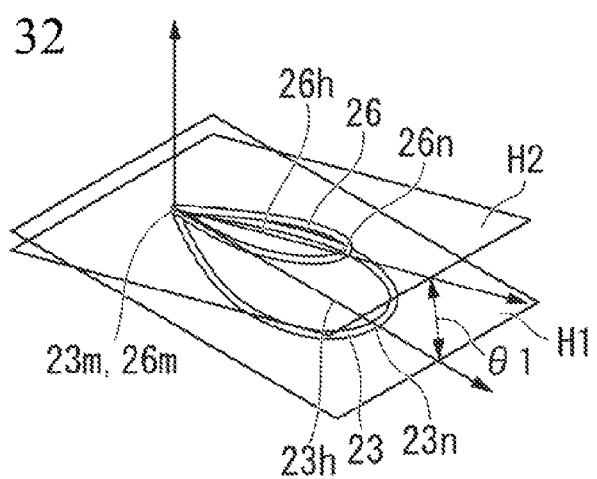
FIG. 32 is a perspective view schematically showing a grasping member of a fourth modified example of the second embodiment of the present invention.

FIG. 32 is a perspective view schematically showing one grasping member of a fourth modified example of the second embodiment.

As shown in FIG. 32, in the modified example, the plane H1 including the main loop wire 23 and the plane H2 including the auxiliary loop wire 26 have a relation in which they form an inclined angle θ1. In the modified example, the centerline 23h of the main loop wire 23 and the centerline 26h of the auxiliary loop wire 26 are formed at a position overlapping when seen in a direction perpendicular to the plane H1 including the main loop wire 23.

Fifth Modified Example of Second Embodiment

Figure 33:
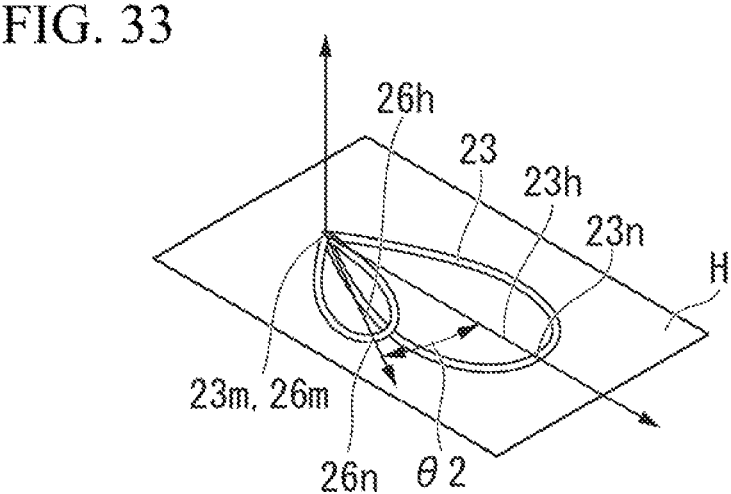
FIG. 33 is a perspective view schematically showing a grasping member of a fifth modified example of the second embodiment of the present invention.

FIG. 33 is a perspective view schematically showing one grasping member of a fifth modified example of the second embodiment.

As shown in FIG. 33, in the modified example, the centerline 23h of the main loop wire 23 and the centerline 26h of the auxiliary loop wire 26 are deviated by an angle θ2 only when seen in a direction perpendicular to the plane H including the main loop wire 23. In the above-mentioned configuration, the same effect as the above-mentioned embodiment is exhibited.

Sixth Modified Example of Second Embodiment

Figure 34:
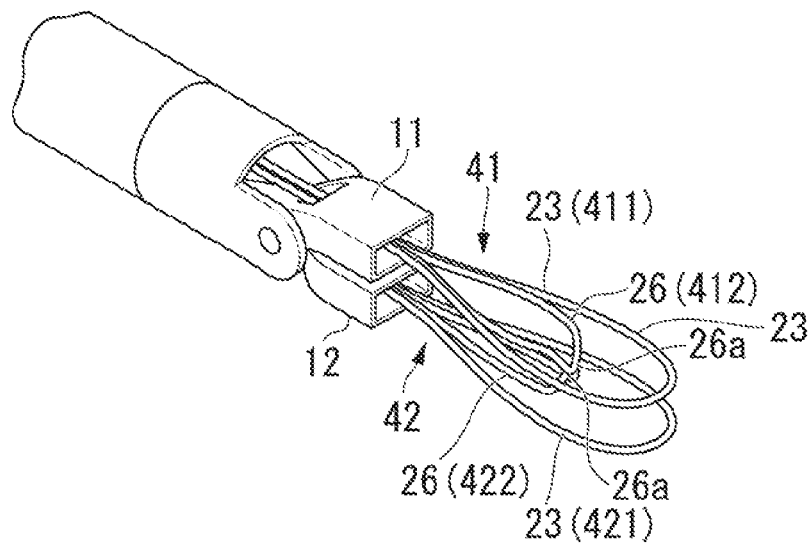
FIG. 34 is a perspective view schematically showing a sixth modified example of the second embodiment of the present invention.
Figure 35:
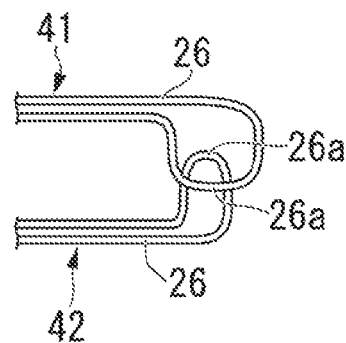
FIG. 35 is a perspective view schematically showing a relation between a pair of auxiliary grasping members of the sixth modified example of the second embodiment of the present invention.

FIG. 34 is a perspective view schematically showing a sixth modified example of the second embodiment. FIG. 34 is a perspective view schematically showing a relation between a pair of auxiliary grasping members (auxiliary loop wires) of the modified example. FIG. 35 is a perspective view schematically showing a relation between the pair of auxiliary grasping members (auxiliary loop wires) of the modified example.

As shown in FIG. 34, in the modified example, a convex portion 26a protruding at a grasp side with respect to the object to be grasped is installed at at least one of the auxiliary loop wires 26 that constitute the respective grasping members 41 and 42. A position of the convex portion 26a is not limited as long as the position is on the auxiliary loop wire 26.

As shown in FIG. 35, a height of the convex portion 26a on the auxiliary loop wire 26 may be a height at which the pair of grasping members 41 and 42 overlap the convex portions 26a of opposite sides when the pair of grasping members 41 and 42 are closed.

Figure 36:
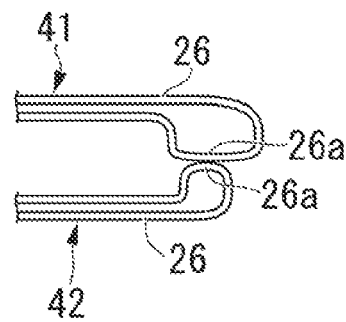
FIG. 36 is a perspective view schematically showing the relation between the pair of auxiliary grasping members of the sixth modified example of the second embodiment of the present invention.

Alternatively, as shown in FIG. 36, the height of the convex portion 26a on the auxiliary loop wire 26 may be a height at which the pair of grasping members 41 and 42 approach the convex portions 26a of the opposite sides when the pair of grasping members 41 and 42 are closed.

Seventh Modified Example of Second Embodiment

Figure 37:
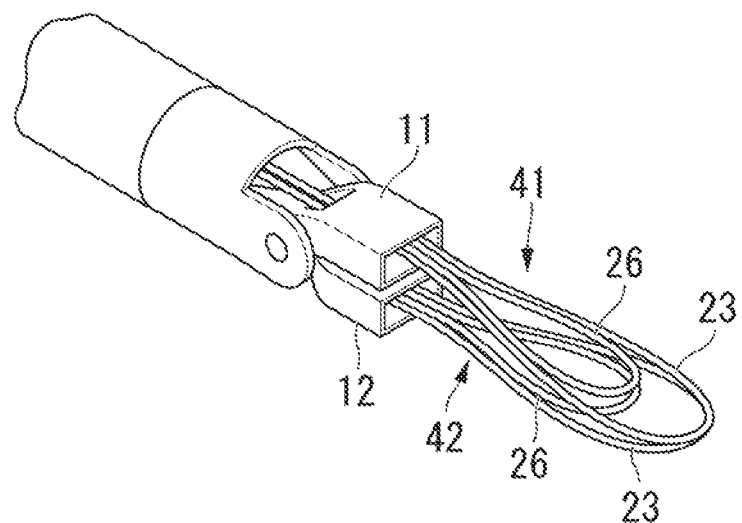
FIG. 37 is a perspective view schematically showing a seventh modified example of the second embodiment of the present invention.

FIG. 37 is a perspective view schematically showing a seventh modified example of the second embodiment.

As shown in FIG. 37, in the modified example, when the pair of grasping members 41 and 42 are closed, the main loop wire 23 and the auxiliary loop wire 26 of the grasping members 41 and 42 are set to incline to further inside than the jaws 11 and 12.

Further, even when the auxiliary loop wire 26 is omitted, the same example is presented. That is, in the grasping member of this example in which only the main loop wire 23 is installed, when the pair of grasping members are closed, the main loop wire is set to incline to a position further inside than the position of the jaw.

Eighth Modified Example of Second Embodiment

Figure 38:
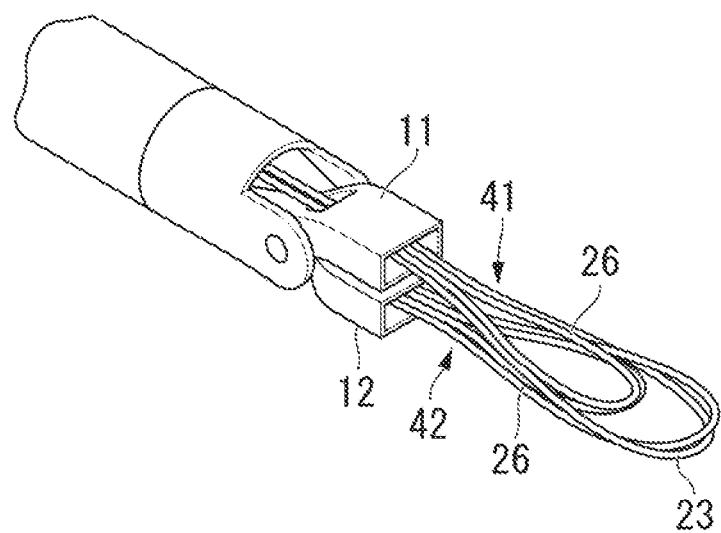
FIG. 38 is a perspective view schematically showing an eighth modified example of the second embodiment of the present invention.

FIG. 38 is a perspective view schematically showing an eighth modified example of the second embodiment.

As shown in FIG. 38, in the modified example, when the pair of grasping members 41 and 42 are closed, the main loop wire 23 and the auxiliary loop wire 26 of the grasping members 41 and 42 are configured to enter the loops of the opposite sides (a space inside of the loop shape). That is, the main loop wire 23 and the auxiliary wire 26 of the first grasping member 41 enter the loops of the main loop wire 23 and the auxiliary loop wire 26 of the second grasping member 42. Alternatively, the main loop wire 23 of the first grasping member 41 enters the loop of the main loop wire 23 of the second grasping member 42. Alternatively, the auxiliary loop wire 26 of the first grasping member 41 is configured to enter the loop of the auxiliary loop wire 26 of the second grasping member 42.

Further, even when the auxiliary loop wire 26 is omitted, the same example may be presented. That is, there is an example in which, when the grasping member having only the main loop wire 23 is closed, the main loop wire of the first grasping member 41 is set to enter the loop of the main loop wire of the second grasping member 42.

Third Embodiment

Next, an endoscopic device 1C according to a third embodiment of the present invention will be described.

Figure 39:
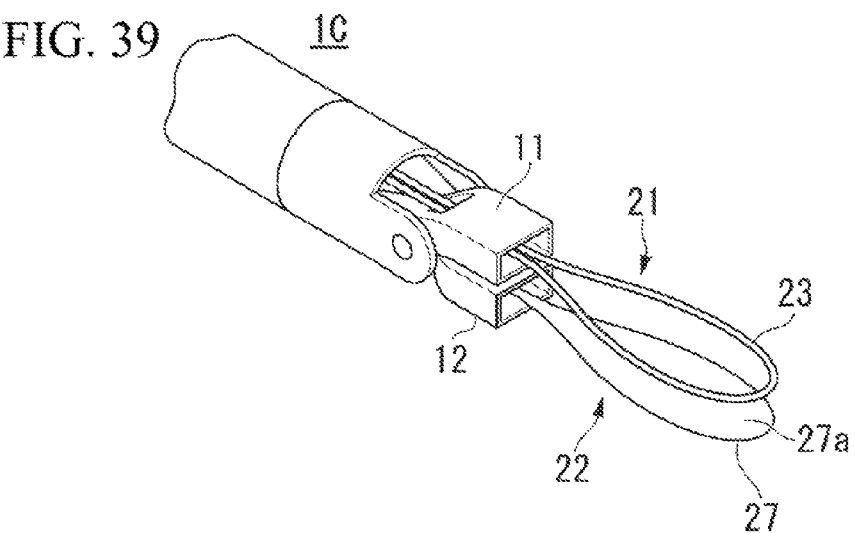
FIG. 39 is a perspective view showing a schematic configuration of a treatment portion of a distal end of an endoscopic device according to a third embodiment of the present invention.

FIG. 39 is a perspective view showing a schematic configuration of the third embodiment of the present invention. In the endoscopic device 1C of the embodiment, the first grasping member 21 is constituted by the loop wire 23. Meanwhile, the second grasping member 22 is constituted by the plate-shaped member 27 having a grasping surface 27a crossing the open-close direction of the pair of jaws 11 and 12. A plate-shaped member 27 is a member such as a lancet.

Fourth Embodiment

Next, an endoscopic device 1D of a fourth embodiment of the present invention will be described.

Figure 40:
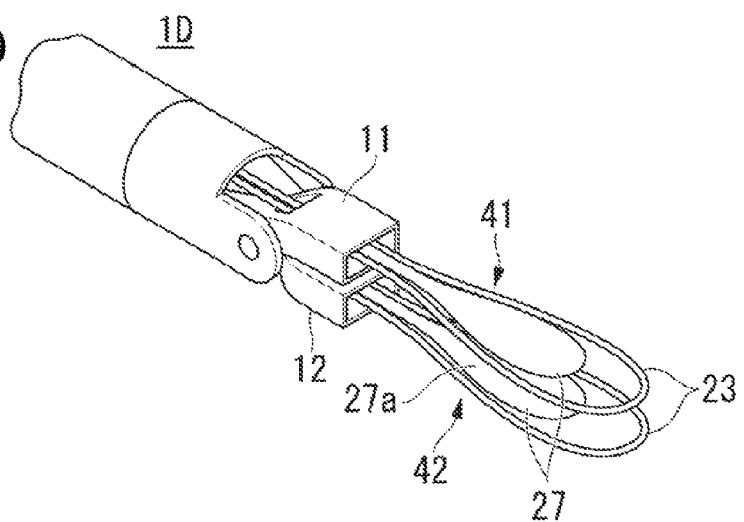
FIG. 40 is a perspective view showing a schematic configuration of a treatment portion of a distal end of an endoscopic device according to a fourth embodiment of the present invention.

FIG. 40 is a perspective view showing a schematic configuration of the fourth embodiment of the present invention. In the endoscopic device 1D according to the embodiment, instead of the auxiliary wire 26 according to the second embodiment, the plate-shaped member 27 having the grasping surface 27a crossing the open-close direction of the pair of jaws 11 and 12 is used.

Fifth Embodiment

Next, an endoscopic device 1E according to a fifth embodiment of the present invention will be described.

Figure 41:
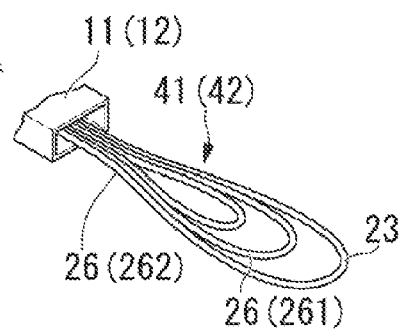
FIG. 41 is a perspective view showing a schematic configuration of a treatment portion of a distal end of an endoscopic device according to a fifth embodiment of the present invention.

FIG. 41 is a perspective view showing a schematic configuration of the endoscopic device 1E according to the fifth embodiment of the present invention. In the endoscopic device 1E according to the embodiment, two or more of the auxiliary wires 26 of the second embodiment are installed. In this way, the number of auxiliary wires 26 may be any number. In addition, it is possible to arbitrarily determine whether the size of the loop of the main wire 23 or the auxiliary wire 26 can be increased or decreased or can freely advance or retreat.

Sixth Embodiment

Next, an endoscopic device 1F according to a sixth embodiment of the present invention will be described.

Figure 42:
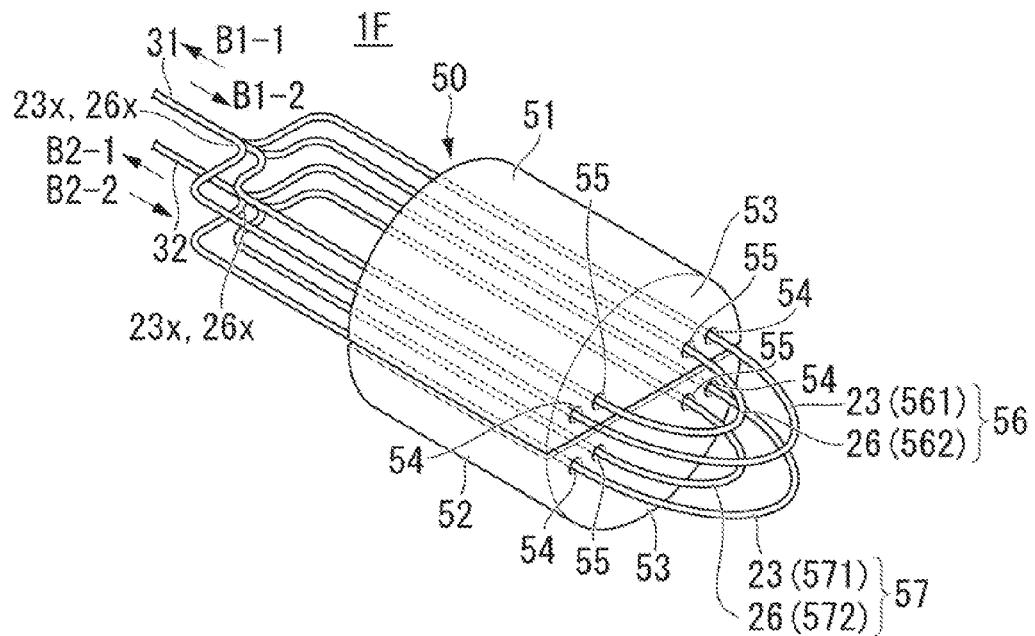
FIG. 42 is a view showing a configuration of a treatment portion of a distal end of an endoscopic device according to a sixth embodiment of the present invention, i.e., a perspective view showing a state in which a pair of jaws are closed.
Figure 43:
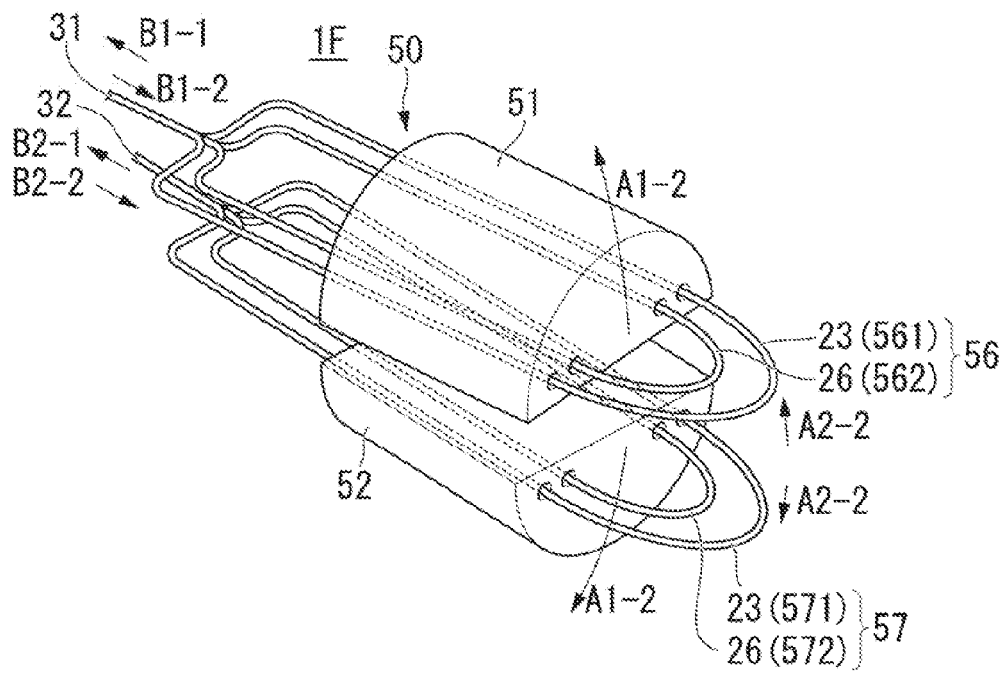
FIG. 43 is a view showing a configuration of the treatment portion of the distal end of the endoscopic device according to the sixth embodiment of the present invention, i.e., a perspective view showing a state in which the pair of jaws are opened.

FIGS. 42 and 43 are views showing a configuration of a treatment portion of a distal end of the endoscopic device 1F of the sixth embodiment. FIG. 42 is a perspective view showing a state in which a pair of jaws are closed. FIG. 43 is a perspective view showing a state in which the pair of jaws are opened.

As shown in FIGS. 42 and 43, a treatment portion 50 of the endoscopic device 1F of the embodiment has a pair of jaws 51 and 52 having a semi-circular columnar shape so as to form a circular columnar body when the two jaws contact with each other. Four through-holes 54 and 55 passing through to the proximal end surfaces of the jaws 51 and 52 are formed in distal end surfaces 53 of the jaws 51 and 52, and a pair of grasping members 56 and 57 are inserted therethrough.

In the embodiment, the pair of grasping members 56 and 57 (a first grasping member 56 and a second grasping member 57) are constituted by sets of two kinds of grasping members which are positioned at an outward of the grasping members and an inward of the grasping members. The grasping members positioned at the outward thereof are main grasping members 561 and 571. The grasping members positioned at the inward thereof are auxiliary grasping members 562 and 572. The auxiliary grasping members 562 and 572 positioned at the inward of the grasping members in an enlarged state are formed to be smaller than the main grasping members 561 and 571 positioned at the outward of the grasping members.

Each of the main grasping members 561 and 571 positioned at the outward of the grasping members and the auxiliary grasping members 562 and 572 positioned at the inward of the grasping members is constituted by half loop wires 23 and 26 curved in a half loop shape. A size of a half loop of an auxiliary half loop wire (an auxiliary wire) 26 in which the size of the half loop is formed to be small is formed to be smaller than a half loop of a main half loop wire (a main wire) 23. The auxiliary half loop wire 26 is disposed to be spaced apart from an inner side of the main half loop wire 23 positioned at the outward of the grasping members.

The main half loop wire 23 and the auxiliary half loop wire 26 are curved in half loop shapes. The main half loop wire 23 and the auxiliary half loop wire 26 are formed such that both ends of the wires 23 and 26 are inserted into the through-holes 54 and 55 formed at the distal end surfaces of the jaws 51 and 52 to extend at the same longitudinal member (not shown) as the longitudinal member 3 shown in FIG. 2.

The main half loop wire 23 and the auxiliary half loop wire 26 are installed to freely advance in a direction protruding from the jaws 51 and 52 and retreat in a direction accommodated in the jaws 51 and 52. The half loop wires 23 and 26 are installed at the pair of jaws 51 and 52 to independently and freely advance and retreat. Accordingly, the half loop wires 23 and 26 are configured to independently and freely enlarge or reduce the size of the half loop within the plane crossing the open-close direction of the jaws 51 and 52 according to the advance and retreat operation of the half loop wires 23 and 26.

According to the endoscopic device 1F of the embodiment, the same effect as the endoscopic device 1B of the second embodiment is exhibited.

Seventh Embodiment

Next, an endoscopic device 1G according to a seventh embodiment of the present invention will be described.

Figure 44:
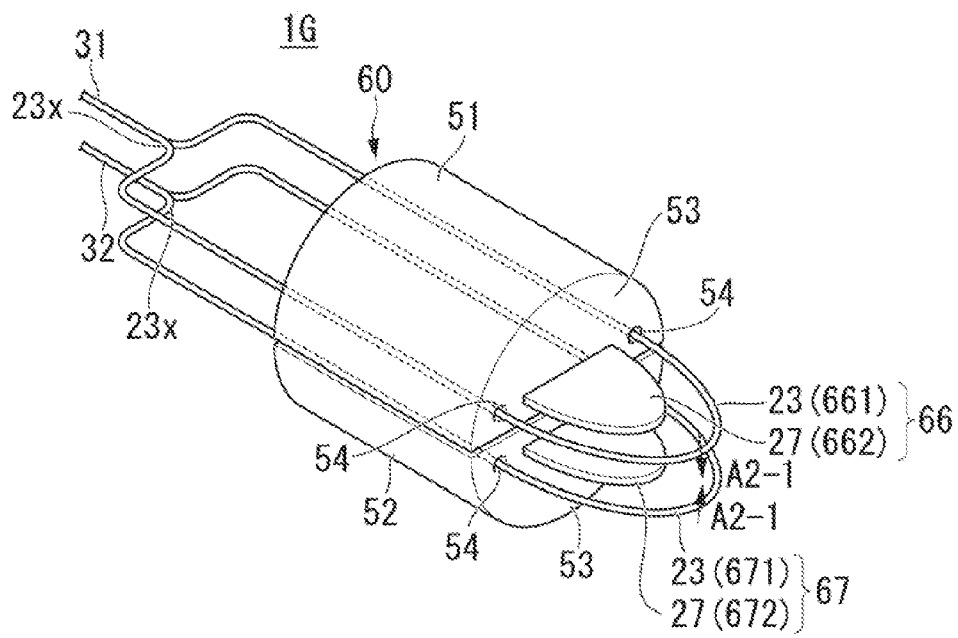
FIG. 44 is a view showing a configuration of a treatment portion of a distal end of an endoscopic device according to a seventh embodiment of the present invention, i.e., a perspective view showing a state in which a pair of jaws are closed.
Figure 45:
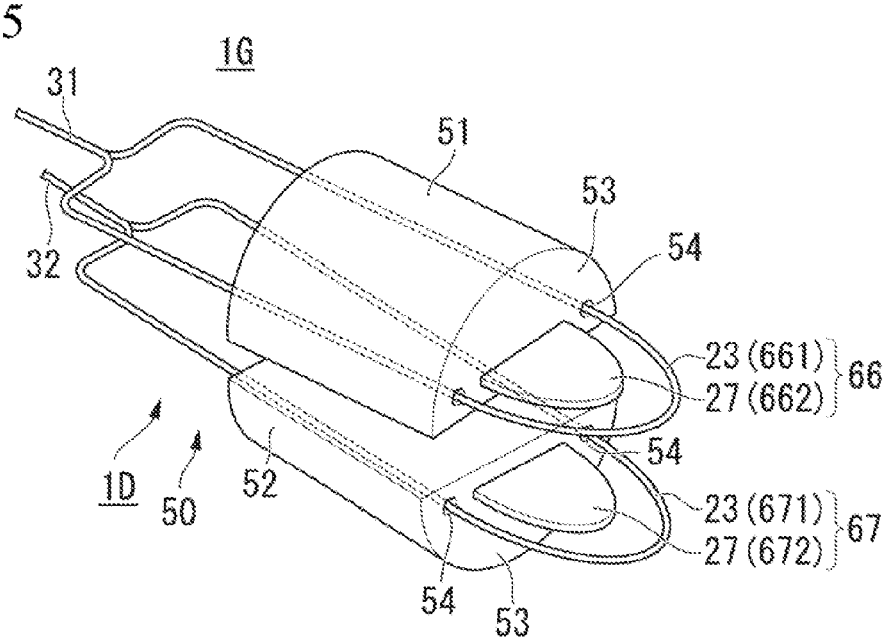
FIG. 45 is a view showing the configuration of the treatment portion of the distal end of the endoscopic device according to the seventh embodiment of the present invention, i.e., a perspective view showing a state in which the pair of jaws are opened.

FIGS. 44 and 45 are views showing a configuration of a treatment portion 60 of a distal end of the endoscopic device 1G of the seventh embodiment. FIG. 44 is a perspective view showing a state in which a pair of jaws are closed. FIG. 45 is a perspective view showing a state in which the pair of jaws are opened.

In the endoscopic device 1G according to the embodiment, a combination of main grasping members 661 and 671 and auxiliary grasping members 662 and 672 of a first grasping member 66 and a second grasping member 67 supported by a first jaw 51 and a second jaw 52 is different from the sixth embodiment. That is, while the main grasping members 661 and 671 are constituted by the same loop wires 23 as in the sixth embodiment, the auxiliary grasping members 662 and 672 are constituted by the plate-shaped members 27 directly protruding from the distal end surfaces of the jaws 51 and 52.

In this way, when the auxiliary grasping members 662 and 672 are constituted by the plate-shaped members 27, a large tissue is grasped by the loop wires 23 of the main grasping members 661 and 671 positioned at the outward of the grasping members, and a small tissue is grasped by the plate-shaped members 27 of the auxiliary grasping members 662 and 672 positioned at the inward of the grasping members. The other effects are the same as those of the sixth embodiment.

Eighth Embodiment

Figure 46:
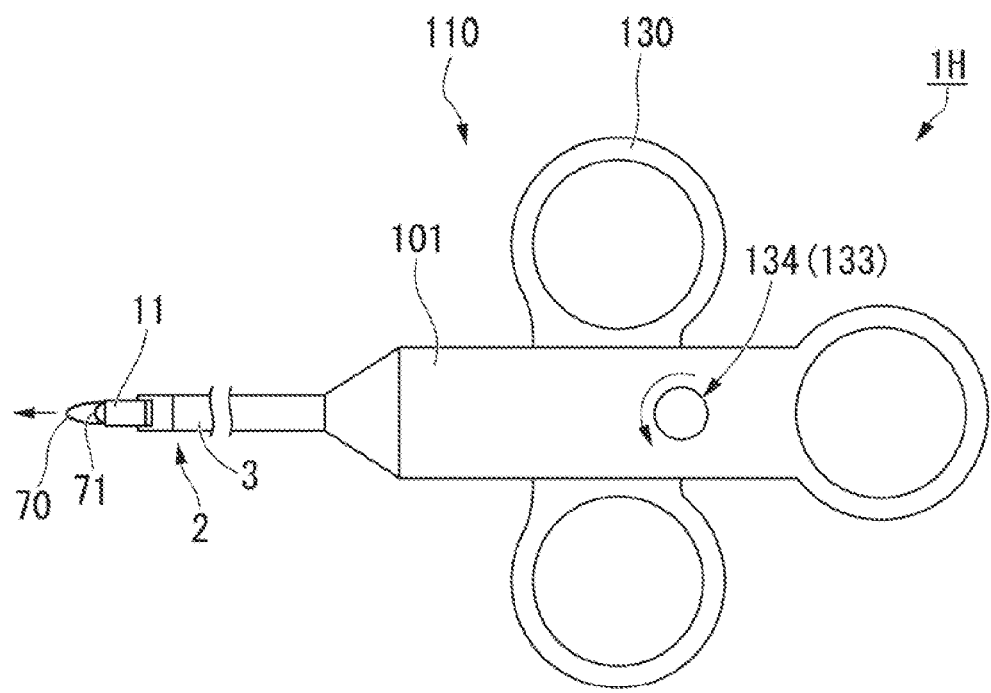
FIG. 46 is a plan view of an endoscopic device according to an eighth embodiment of the present invention.
Figure 47:
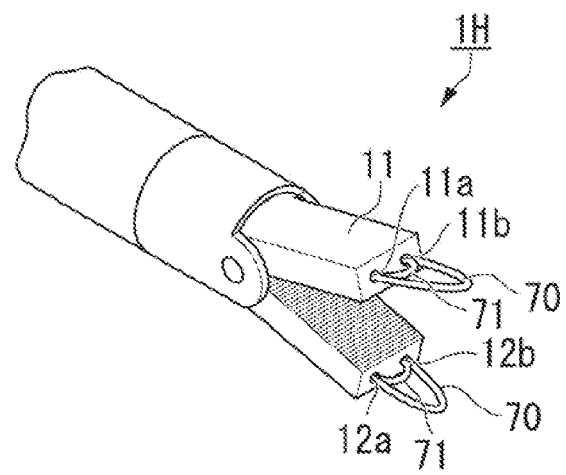
FIG. 47 is a perspective view showing a distal end structure of an endoscopic device according to the eighth embodiment of the present invention.
Figure 48:
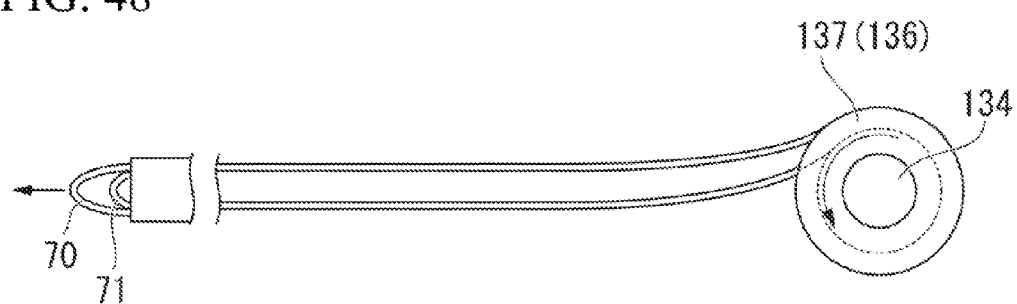
FIG. 48 is a plan view showing a configuration of a pulley group of the endoscopic device according to the eighth embodiment of the present invention.
Figure 49:
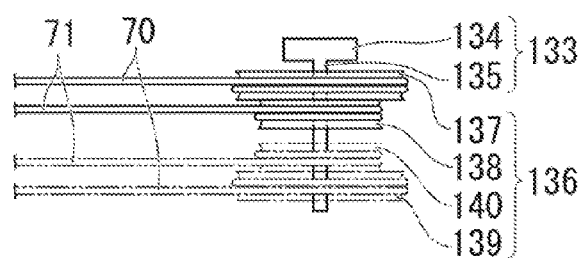
FIG. 49 is a side view showing the configuration of the pulley group of the endoscopic device according to the eighth embodiment of the present invention.

Next, an endoscopic device 1H according to an eighth embodiment of the present invention will be described. FIG. 46 is a plan view of the endoscopic device 1H according to the embodiment. FIG. 47 is a perspective view of a distal end structure of the endoscopic device 1H according to the embodiment. FIG. 48 is a plan view showing a configuration of a pulley group of the endoscopic device 1H according to the embodiment. FIG. 49 is a side view showing a configuration of the pulley group of the endoscopic device 1H according to the embodiment.

As shown in FIG. 46, the endoscopic device 1H according to the embodiment has a main loop wire 70 and an auxiliary loop wire 71 having different configurations from the main loop wire 23 and the auxiliary loop wire 26, instead of the main loop wire 23 and the auxiliary loop wire 26 described in the second embodiment.

In addition, as shown in FIG. 47, through-holes 11a and 12a into which the main loop wire 70 is inserted to freely advance and retreat and through-holes 11b and 12b into which the auxiliary loop wire 71 is inserted to freely advance and retreat are formed in the jaws 11 and 12. Further, the endoscopic device 1H according to the embodiment has an operating portion 110 having a different configuration from the operating portion 100, instead of the operating portion 100 described in the first embodiment.

The main loop wires 70 are installed at each of the first jaw 11 and the second jaw 12.

A first end of the main loop wire 70 installed at the jaw 11 is fixed to a portion of the distal end of the jaw 11. A second end of the main loop wire 70 installed at the jaw 11 is connected to the operating portion 110. In the embodiment, the first end of the main loop wire 70 installed at the jaw 11 enters the through-hole 11b into which the auxiliary loop wire 71 is inserted to freely advance and retreat, and the first end of the main loop wire 70 is fixed to the jaw 11 in the through-hole 11b.

The first end of the main loop wire 70 installed at the jaw 12 is fixed to a portion of the distal end of the jaw 12. The second end of the main loop wire 70 installed at the jaw 12 is connected to the operating portion 110. In the embodiment, the first end of the main loop wire 70 installed at the jaw 12 enters the through-hole 12b into which the auxiliary loop wire 71 is inserted to freely advance and retreat, and the first end of the main loop wire 70 is fixed to the jaw 12 in the through-hole 12b.

The auxiliary loop wires 71 are installed at each of the jaw 11 and the jaw 12. A first end of the auxiliary loop wire 71 installed at the jaw 11 is fixed to a portion of the distal end of the jaw 11. A second end of the auxiliary loop wire 71 installed at the jaw 11 is connected to the operating portion 110. In the embodiment, the first end of the auxiliary loop wire 71 installed at the jaw 11 enters a through-hole 11a into which the main loop wire 70 is inserted to freely advance and retreat, and the first end of the auxiliary loop wire 71 is fixed to the jaw 11 in the through-hole 11a.

The first end of the auxiliary loop wire 71 installed at the jaw 12 is fixed to a portion of the distal end of the jaw 12. The second end of the auxiliary loop wire 71 installed at the jaw 12 is connected to the operating portion 110. In the embodiment, the first end of the auxiliary loop wire 71 installed at the jaw 12 enters a through-hole 12a into which the main loop wire 70 is inserted to freely advance and retreat, and the first end of the auxiliary loop wire 71 is fixed to the jaw 11 in the through-hole 12a.

The operating portion 110 shown in FIG. 46 has a manipulation knob 133 instead of the manipulation members 131 and 132 with respect to the operating portion main body 101 described in the first embodiment.

As shown in FIGS. 46, 48 and 49, the manipulation knob 133 is a substantially columnar member attached to the operating portion main body 101 such that a rotational center extends in a direction perpendicular to the longitudinal axis of the operating portion main body 101. In the manipulation knob 133, a dial 134 is installed at a portion of the operating portion main body 101 exposed to the outside. The dial 134 is configured such that the operator can touch the dial 134 to rotate the manipulation knob 133. A rotary shaft 135 and a pulley group 136 are installed at a portion of the manipulation knob 133 disposed inside the operating portion main body 101. The rotary shaft 135 is fixed to the dial 134 or integrally formed with the dial 134. The pulley group 136 is fixed to the rotary shaft 135 such that a rotational axis of the rotary shaft 135 serves as a rotational center.

Large diameter pulleys (first movable members) 137 and 139 and small diameter pulleys (second movable members) 138 and 140 are installed at the pulley group 136. The main loop wire 70 is suspended on outer circumferences of the large diameter pulleys 137 and 139. The auxiliary loop wire 71 is suspended on outer circumferences of the small diameter pulleys 138 and 140.

The large diameter pulley 137 is a pulley having a radius larger than that of the small diameter pulley 138. The large diameter pulley 139 is a pulley having a radius larger than that of the small diameter pulley 140. In addition, in the embodiment, the radiuses of the two large diameter pulleys 137 and 139 are equal to each other, and the radiuses of the two small diameter pulleys 138 and 140 are equal to each other.

The second end of the main loop wire 70 installed at the first jaw 11 is fixed to the first large diameter pulley 137 of the two large diameter pulleys 137 and 138. The second end of the main loop wire 70 installed at the jaw 12 is fixed to the second large diameter pulley 139. The direction in which the main loop wire 70 is wound on the first large diameter pulley 137 is the same as the direction in which the main loop wire 70 is wound on the second large diameter pulley 139.

The second end of the auxiliary loop wire 71 installed at the first jaw 11 is fixed to the first small diameter pulley 138 of the two small diameter pulleys 138 and 140. The second end of the auxiliary loop wire 71 installed at the jaw 12 is fixed to the second small diameter pulley 140. The direction in which the auxiliary loop wire 71 is wound on the first small diameter pulley 138 is the same as the direction in which the auxiliary loop wire 71 is wound on the second small diameter pulley 140.

In the embodiment, the direction in which the main loop wire 70 is wound on the first large diameter pulley 137, the direction in which the main loop wire 70 is wound on the second large diameter pulley 139, the direction in which the auxiliary loop wire 71 is wound on the first small diameter pulley 138 and the direction in which the auxiliary loop wire 71 is wound on the second small diameter pulley 140 are all the same. Further, the large diameter pulleys 137 and 139 and the small diameter pulleys 138 and 140 are integrally rotated with the rotary shaft 135 when the rotary shaft 135 is rotated about the rotational axis thereof as a rotational center. For this reason, when the dial 134 is rotated by the operator, the pulley group 136 moves the two main loop wires 70 and the two auxiliary loop wires 71 to advance and retreat such that the sizes of the entire loops protruding from the jaws 11 and 12 become larger or the sizes of the entire loops protruding from the jaws 11 and 12 become smaller.

Figure 50:
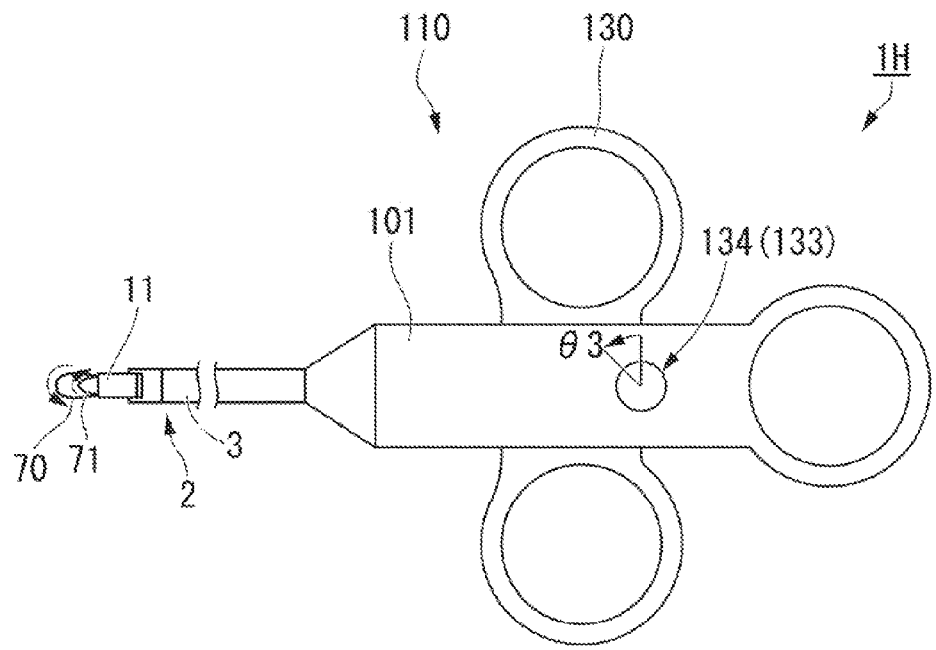
FIG. 50 is a view showing an action of the endoscopic device according to the eighth embodiment of the present invention.
Figure 51:
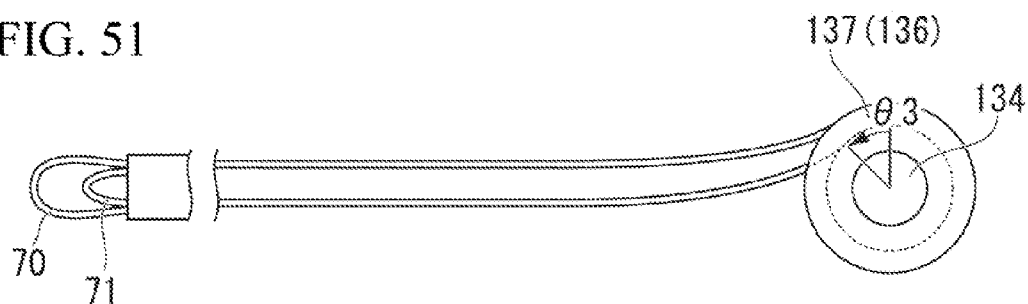
FIG. 51 is a plan view showing an action of the pulley group of the endoscopic device according to the eighth embodiment of the present invention.
Figure 52:
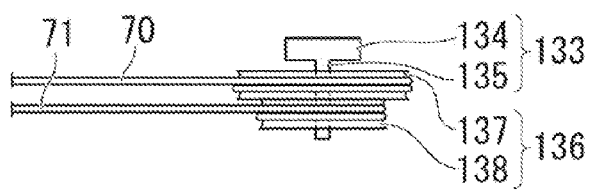
FIG. 52 is a side view showing the action of the pulley group of the endoscopic device according to the eighth embodiment of the present invention.

An action of the endoscopic device 1H according to the embodiment will be described. FIG. 50 is a view showing the action of the endoscopic device 1H according to the embodiment. FIG. 51 is a plan view showing an action of the pulley group of the endoscopic device according to the embodiment. FIG. 52 is a side view showing the action of the pulley group of the endoscopic device of the embodiment.

In the embodiment, when the manipulation knob 133 is rotated about the rotational center by a certain angle θ3, a protrusion length from the jaws 11 and 12 of the main loop wire 70 attached to the large diameter pulleys 137 and 139 is larger than a protrusion length from the jaws 11 and 12 of the auxiliary loop wire 71 attached to the small diameter pulleys 138 and 140. In addition, since the radiuses of the two large diameter pulleys 137 and 139 are equal to each other, the protrusion length of the main loop wire 70 from the jaw 11 and the protrusion length of the main loop wire 70 from the jaw 12 are equal to each other. Further, since the radiuses of the two small diameter pulleys 138 and 140 are equal to each other, the protrusion length of the auxiliary loop wire 71 from the jaw 11 and the protrusion length of the auxiliary loop wire 71 from the jaw 12 are equal to each other.

Accordingly, in the embodiment, when the operator rotates the dial 134 in a state in which a relation that the size of the loop of the main loop wire 70 is always larger than that of the loop of the auxiliary loop wire 71 is maintained, the sizes of the loop by the main loop wire 70 and the loop by the auxiliary loop wire 71 can be modified. According to the endoscopic device 1H of the embodiment, a loop shape having the best operational efficiency can be selected to correspond to characteristics of the tissue serving as the collecting target.

First Modified Example of Eighth Embodiment

Figure 53:
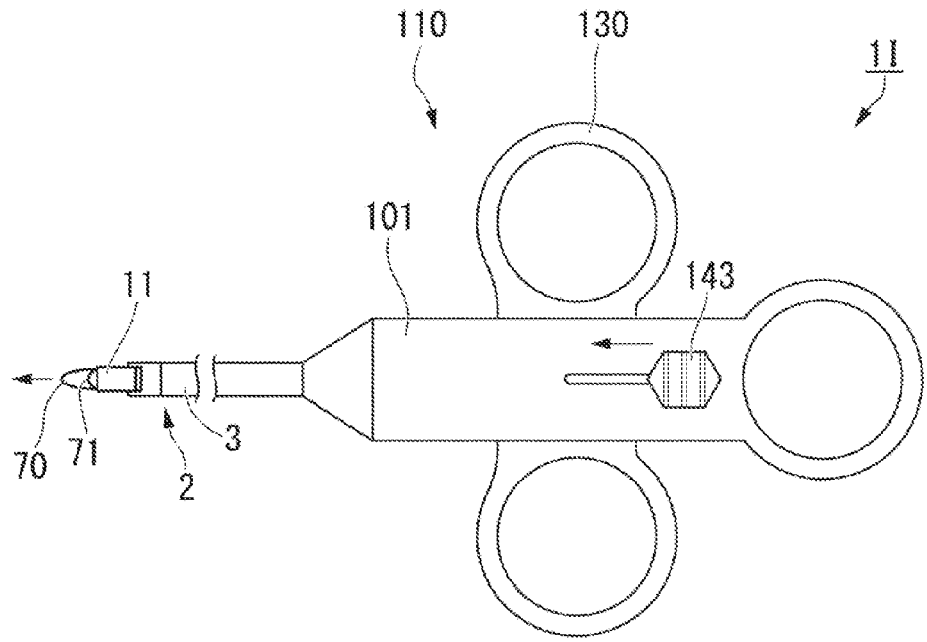
FIG. 53 is a plan view showing an endoscopic device of a first modified example of the eighth embodiment of the present invention.
Figure 54:
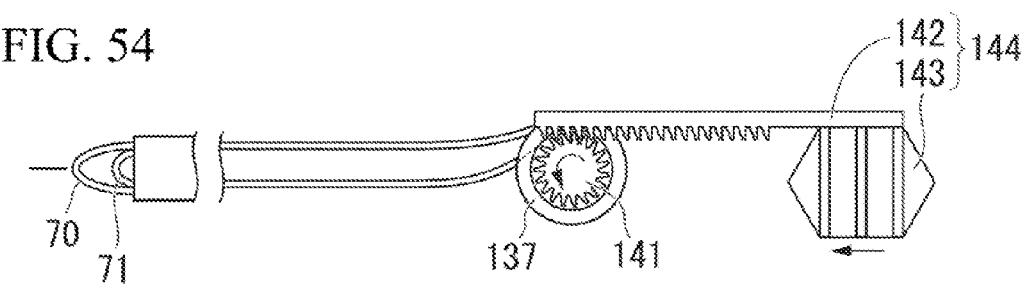
FIG. 54 is a schematic plan view showing a configuration of a pinion, a rack and a slider of the endoscopic device of the modified example of the eighth embodiment of the present invention.
Figure 55:
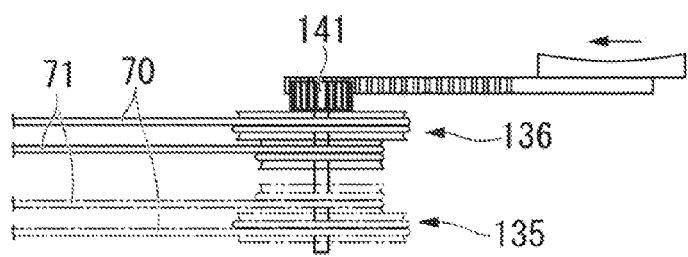
FIG. 55 is a schematic side view showing the configuration of the pinion, the rack and the slider of the endoscopic device of the modified example of the eighth embodiment of the present invention.
Figure 56:
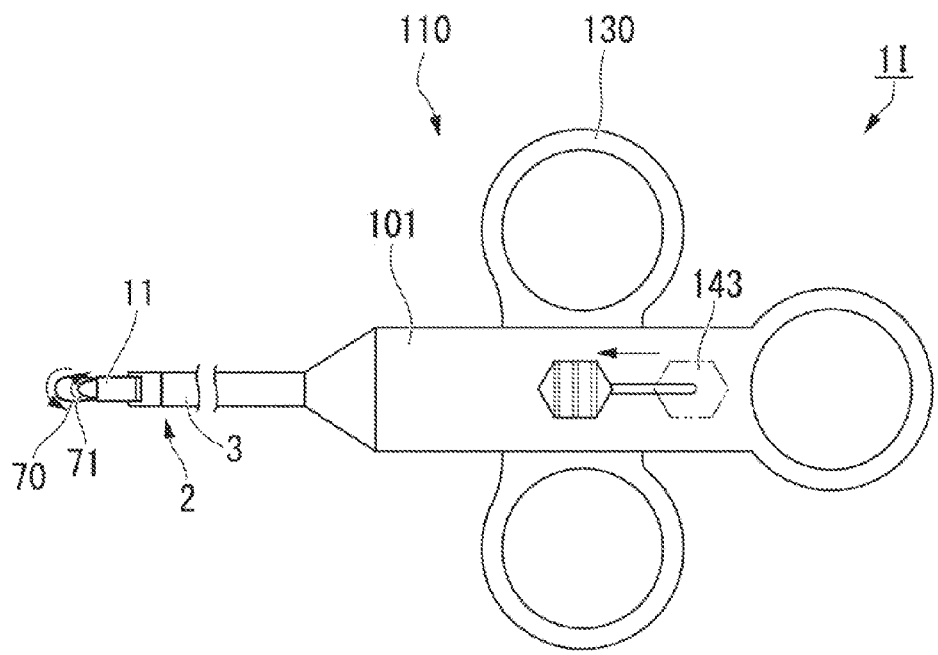
FIG. 56 is a view showing an action of the endoscopic device of the modified example of the eighth embodiment of the present invention.
Figure 57:
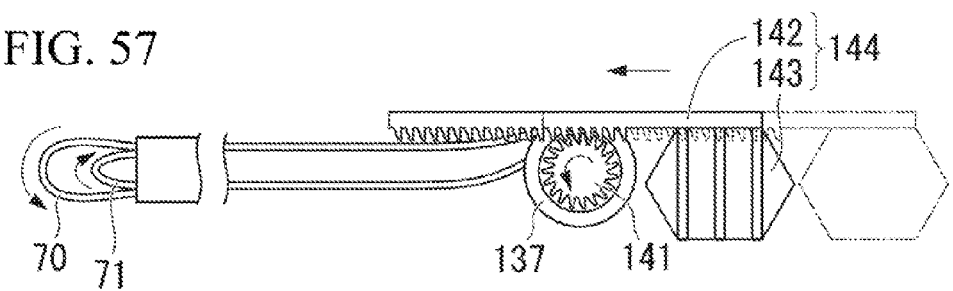
FIG. 57 is a view showing an action of the endoscopic device of the modified example of the eighth embodiment of the present invention.
Figure 58:
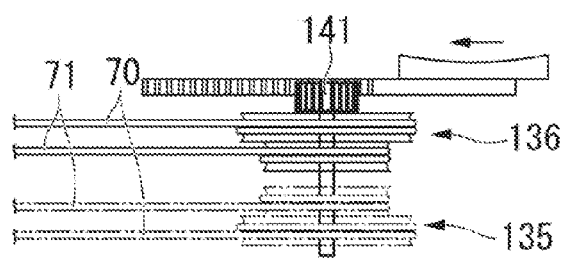
FIG. 58 is a view showing the action of the endoscopic device of the modified example of the eighth embodiment of the present invention.

Next, a first modified example of the embodiment will be described. FIG. 53 is a plan view showing an endoscopic device of the modified example. FIG. 54 is a schematic plan view showing a configuration of a pinion, a rack and a slider of the endoscopic device of the modified example. FIG. 55 is a schematic side view showing the configuration of the pinion, the rack and the slider of the endoscopic device of the modified example. FIGS. 56 to 58 are views showing an action of the endoscopic device of the modified example.

As shown in FIGS. 53 to 55, an endoscopic device 1I of the modified example includes a pinion 141 fixed to the rotary shaft 135 and a slider 144, instead of the manipulation knob 133 described in the eighth embodiment. The slider 144 has a rack 142 meshed with the pinion 141, and a portion to be grasped 143 fixed to the rack 142.

In the rack 142 formed at the slider 144, a lengthwise direction of the rack 142 is disposed in the operating portion main body 101 along a lengthwise direction of the operating portion main body 101. The portion to be grasped 143 disposed at the slider 144 is disposed outside the operating portion main body 101. The portion to be grasped 143 is grasped by the operator, and moved to advance and retreat by the operator in the lengthwise direction of the operating portion main body 101.

In the modified example, as shown in FIGS. 56 to 58, as the portion to be grasped 143 is manipulated by the operator to advance and retreat, the rack 142 rotates the pinion 141, and thus the pulley group 136 is integrally rotated therewith. Accordingly, the endoscopic device 1I of the modified example exhibits the same effects as the endoscopic device 1H described in the eighth embodiment.

Ninth Embodiment

Figure 59:
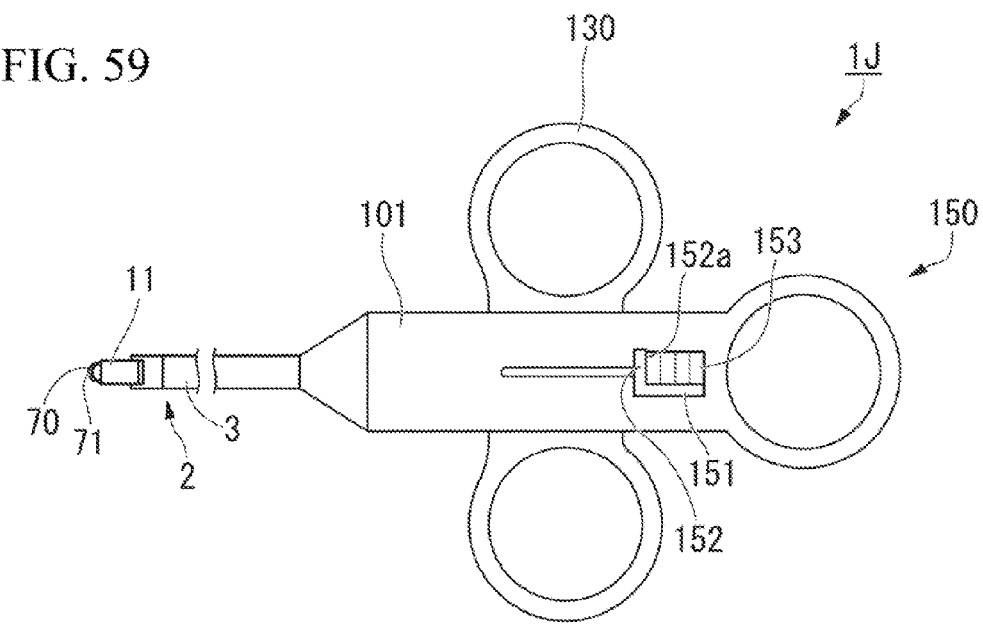
FIG. 59 is a plan view showing an endoscopic device according to a ninth embodiment of the present invention.
Figure 60:
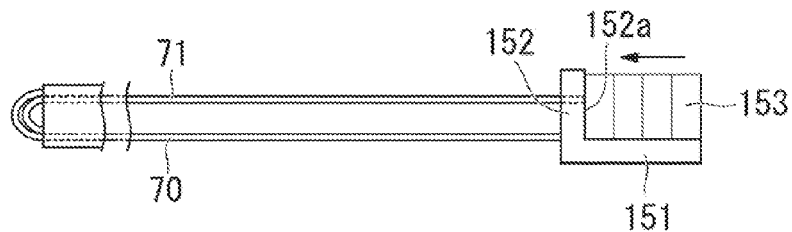
FIG. 60 is a schematic plan view showing an internal structure of an operating portion of the ninth embodiment of the present invention.

Next, an endoscopic device 1J of a ninth embodiment of the present invention will be described. FIG. 59 is a plan view showing the endoscopic device 1J according to the embodiment. FIG. 60 is a schematic plan view showing an internal structure of an operating portion of the endoscopic device 1J according to the embodiment.

As shown in FIG. 59, the endoscopic device 1J according to the embodiment has an operating portion 150 having a different configuration from the operating portion 110, instead of the operating portion 110 described in the eighth embodiment.

As shown in FIGS. 59 and 60, the operating portion 150 has a first slider (a first movable member) 151 and a second slider (a second movable member) 153. The first slider 151 is fixed to the other end of the main loop wire 70, i.e., an end thereof at which the operating portion 150 is disposed. The second slider 153 is fixed to the other end of the auxiliary loop wire 71 (an end thereof at which the operating portion 150 is disposed).

The first slider 151 has a stopper 152 configured to restrict movement of the second slider 153 to a distal end side of the operating portion 150 farther than the first slider 151.

The stopper 152 has a wall (an abutting surface) 152a abutting a wall (a distal end surface) 153a of a distal end of the second slider 153. When the wall 153a of the second slider 153 abuts the wall 152a, the second slider 153 cannot move to the distal end side of the operating portion 150 on its own, except for the case in which the second slider 153 moves with the first slider 151 to the distal end side of the operating portion 150.

If the wall 153a of the distal end of the second slider 153 is in a state that is spaced apart from the wall 152a at the proximal end side farther than the wall 152a, the second slider 153 can freely advance and retreat regardless of the position of the first slider 151.

In the embodiment, when the second slider 153 abuts the wall 152a of the stopper 152 installed at the first slider 151, the sizes of the loops of the main loop wire 70 and the auxiliary loop wire 71 protruding from the jaws 11 and 12 have a relation in which the loop by the main loop wire 70 is larger than the loop by the auxiliary loop wire 71.

In the embodiment, both of the main loop wire 70 installed at the jaw 11 and the main loop wire 70 installed at the jaw 12 are fixed to the first slider 151. Both of the auxiliary loop wire 71 installed at the jaw 11 and the auxiliary loop wire 71 installed at the jaw 12 are fixed to the second slider 153.

Figure 61:
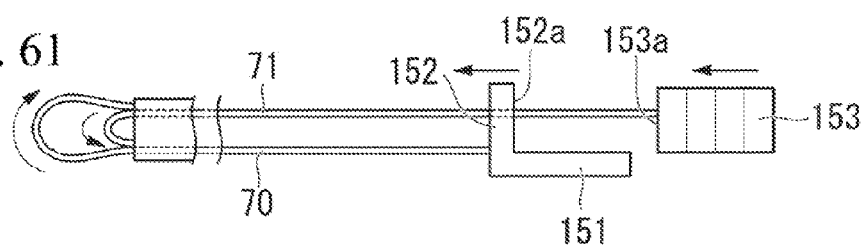
FIG. 61 is a view showing an action of the endoscopic device of the ninth embodiment of the present invention.
Figure 62:
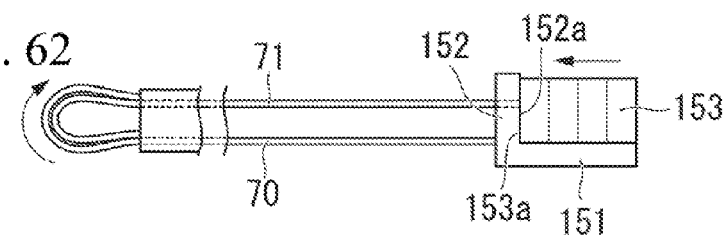
FIG. 62 is a view showing the action of the endoscopic device of the ninth embodiment of the present invention.

An action of the endoscopic device 1J of the embodiment will be described. FIG. 61 is a view showing the action of the endoscopic device 1J according to the embodiment. FIG. 62 is a view showing the action of the endoscopic device 1J according to the embodiment.

As shown in FIGS. 60 to 62, in the embodiment, when the second slider 153 is disposed to be spaced apart from the proximal end side of the first slider 151 (see FIG. 61), the first slider 151 and the second slider 153 are configured to be manipulated to independently advance and retreat. Accordingly, in this state, the sizes of the loop by the main loop wire 70 and the loop by the auxiliary loop wire 71 can be independently varied. In addition, in this state, the size of the loop by the main loop wire 70 is always larger than that of the loop by the auxiliary loop wire 71.

In addition, when the second slider 153 comes in contact with the stopper 152 of the first slider 151 (see FIGS. 60 and 62), movement of the second slider 153 toward the distal end side of the operating portion main body 101 is restricted by the stopper 152 of the first slider 151, and the second slider 153 is configured to enable only movement toward the proximal end side of the operating portion main body 101. Further, integrated movement of the first slider 151 and the second slider 153 in contact with each other in the lengthwise direction of the operating portion main body 101 is not particularly limited.

According to the endoscopic device 1J of the embodiment, the first slider 151 and the second slider 153 can be independently operated to independently vary the size of the loops of the main loop wire 70 and the auxiliary loop wire 71. Further, as the first slider 151 and the second slider 153 are integrally operated in a state in which the second slider 153 abuts the stopper 152 of the first slider 151, the sizes of the loops can be easily varied while approximately a certain difference in the sizes of the loops of the main loop wire 70 and the auxiliary loop wire 71 is maintained.

Tenth Embodiment

Figure 63:
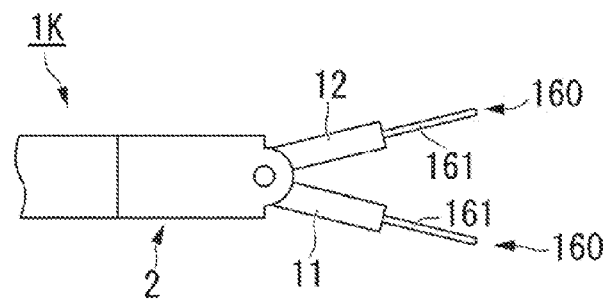
FIG. 63 is a side view showing a distal end structure of an endoscopic device according to a tenth embodiment of the present invention.
Figure 64:
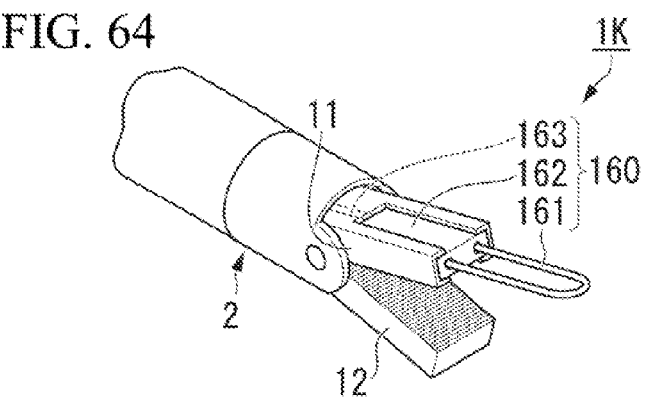
FIG. 64 is a perspective view showing a portion of the distal end structure of the endoscopic device according to the tenth embodiment of the present invention.
Figure 65:
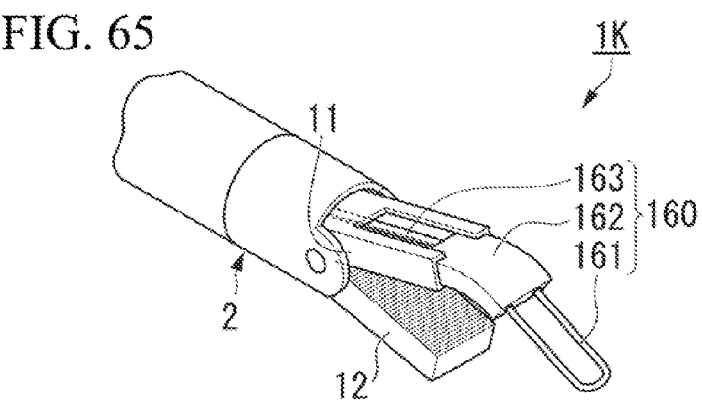
FIG. 65 is a perspective view showing the portion of the distal end structure of the endoscopic device according to the tenth embodiment of the present invention.
Figure 66:
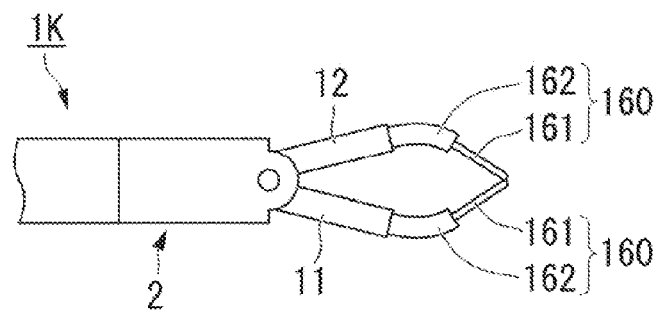
FIG. 66 is a view showing an action of the endoscopic device according to the tenth embodiment of the present invention.

Next, an endoscopic device 1K of a tenth embodiment of the present invention will be described. FIG. 63 is a side view showing a distal end structure of the endoscopic device of the embodiment. FIG. 64 is a perspective view showing a portion of the distal end structure of the endoscopic device of the embodiment. FIG. 65 is a perspective view showing the portion of the distal end structure of the endoscopic device of the embodiment. FIG. 66 is a view showing an action of the endoscopic device of the embodiment.

As shown in FIGS. 63 to 65, the endoscopic device 1K according to the embodiment has two loop wires 160 having a different configuration from the loop wire 23, instead of the loop wire 23 described in the first embodiment.

The two loop wires 160 are installed with respect to the jaw 11 and the jaw 12 one by one. Hereinafter, only a configuration of the loop wire 160 installed at the jaw 11 will be described, and overlapping description of a configuration of the loop wire 160 installed at the jaw 12 will be omitted.

The loop wire 160 has a main loop portion 161, an elastic portion 162, and a manipulation wire portion 163 (manipulation wire). The main loop portion 161 constitutes a loop protruding from the distal end of the jaw 11. The elastic portion 162 is inserted into the jaw 11 to which the main loop portion 161 is fixed. The manipulation wire portion 163 connects the elastic portion 162 and the operating portion 100.

As shown in FIG. 65, the elastic portion 162 installed at the first jaw 11 has a shape such that the distal end thereof is gradually curved toward the second jaw 12 more than the proximal end thereof. As shown in FIG. 64, when the elastic portion 162 is disposed inside the first jaw 11, the elastic portion 162 is pressed against the first jaw 11 to be in an elastically deformed state. As shown in FIG. 65, when the elastic portion 162 is exposed from the first jaw 11, the elastic portion 162 is recovered to the above-mentioned original curved state by a recovering force of the elastic portion 162 in a portion of the elastic portion 162 exposed from the first jaw 11.

As shown in FIG. 66, the elastic portion 162 installed at the second jaw 12 is an elastic member having a shape such that the distal end of the second jaw 12 is gradually curved toward the first jaw 11 more than the proximal end. The elastic portion 162 installed at the second jaw 12 has a different configuration from the elastic portion 162 installed at the first jaw 11 at this point.

The manipulation wire portion 163 is connected to a manipulation member 131 in the operating portion 100 of the endoscopic device 1K (see FIG. 10), and manipulated by the operator to advance and retreat. Further, the manipulation wire portion 163 of the loop wire 160 installed at the second jaw 12 is fixed to the manipulation member 131.

Next, an action of the endoscopic device 1K of the embodiment will be described.

In the endoscopic device 1K according to the embodiment, as the manipulation for advancing and retracting the manipulation members 131 and 132 is performed by the operator, the elastic portion 162 protrudes from each of the jaws 11 and 12, or the elastic portion 162 is accommodated in each of the jaws 11 and 12. As the elastic portion 162 protrudes from each of the jaws 11 and 12 from a state in which the elastic portion 162 is accommodated in each of the jaws 11 and 12, the elastic portion 162 is recovered to the curved shape. As the elastic portion 162 is recovered to the curved state, as shown in FIG. 66, the main loop portions 161 installed at the distal ends of the elastic portions 162 are moved to approach each other.

An operation of the main loop portions 161 approaching each other is an operation of grasping the necrotic tissue during treatment using the endoscopic device 1K. In addition, the manipulation of opening and closing the jaws 11 and 12 is an operation of grasping the necrotic tissue, which is the same action as in the first embodiment. In the embodiment, the operation of the main loop portions 161 approaching each other is used to adjust a difference in the grasping force with which the necrotic tissue is grasped. That is, in a state in which the elastic portion 162 does not protrude from the jaws 11 and 12, a force pressing the necrotic tissue when each of the main loop portions 161 grasps the necrotic tissue is reduced. Meanwhile, in a state in which the elastic portion 162 protrudes from the jaws 11 and 12, the force pressing the necrotic tissue when each of the main loop portion 161 grasps the necrotic tissue is larger than that when the elastic portion 162 does not protrude from the jaws 11 and 12.

In the endoscopic device 1K according to the embodiment, the grasping force required for the tissue serving as the grasping target can be previously set by adjusting the protrusion amount of the elastic portion 162 from the jaws 11 and 12. For this reason, even when different grasping forces are set, manipulation amounts of the manipulation members 131 and 132 are not largely varied.

In the endoscopic device 1K of the embodiment, according to necessity, a direction of each of the main loop portions 161 with respect to the jaws 11 and 12 can be easily varied. For this reason, a collecting operation can be efficiently performed according to the size of the tissue serving as the collecting target.

Eleventh Embodiment

Figure 67:
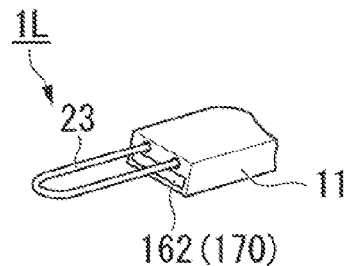
FIG. 67 is a perspective view showing a distal end structure of an endoscopic device according to an eleventh embodiment of the present invention.
Figure 68:
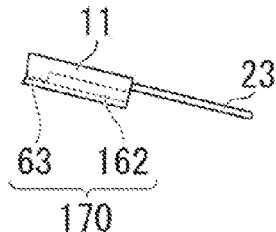
FIG. 68 is a side view showing an action of the endoscopic device according to the eleventh embodiment of the present invention.
Figure 69:
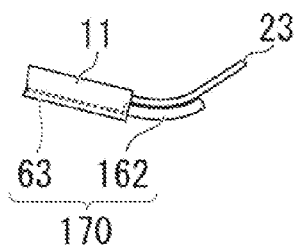
FIG. 69 is a side view showing the action of the endoscopic device according to the eleventh embodiment of the present invention.

Next, an endoscopic device 1L according to an eleventh embodiment of the present invention will be described. FIG. 67 is a perspective view showing a distal end structure of the endoscopic device according to the embodiment. FIG. 68 is a side view showing an action of the endoscopic device according to the embodiment. FIG. 69 is a side view showing the action of the endoscopic device according to the embodiment.

As shown in FIGS. 67 and 68, in the embodiment, a curved portion 170 configured to vary the direction of the loop wire 23 is formed at the jaws 11 and 12 described in the first embodiment. Further, in the embodiment, the curved portion 170 installed at the first jaw 11 and the curved portion 170 installed at the second jaw 12 have the same configuration. Hereinafter, only the curved portion 170 installed at the first jaw 11 will be described in detail, and overlapping descriptions will be omitted.

The curved portion 170 has the elastic portion 162 and the manipulation wire portion 163 described in the tenth embodiment.

The elastic portion 162 of the embodiment is inserted into the first jaw 11 so as to be capable of advancing and retreating. The elastic portion 162 is a separate body from the loop wire 23, and variation of the loop diameter of the loop wire 23 and protrusion of the elastic portion 162 from the first jaw 11 can be independently controlled in the operating portion 100. That is, in the embodiment, in addition to the manipulation member 131 configured to vary the loop diameter of the loop wire 23, a manipulation member (not shown) configured to advance and retreat the manipulation wire portion 163 is further installed at the operating portion 100.

An action of the endoscopic device 1L according to the embodiment will be described.

As shown in FIG. 68, in the embodiment, when the elastic portion 162 is completely accommodated in the first jaw 11, the loop wire 23 does not come in contact with the elastic portion 162. As shown in FIG. 69, when the elastic portion 162 protrudes from the first jaw 11, the elastic portion 162 presses the loop wire 23, and like the tenth embodiment, the loop portion protruding from the first jaw 11 (in the embodiment, the loop wire 23) is curved. Accordingly, even in the endoscopic device 1L of the embodiment, like the endoscopic device 1K described in the tenth embodiment, the direction of the loop formed by the loop wire 23 can be varied, and the grasping force of the tissue by the loop can be appropriately set.

Twelfth Embodiment

Figure 70:
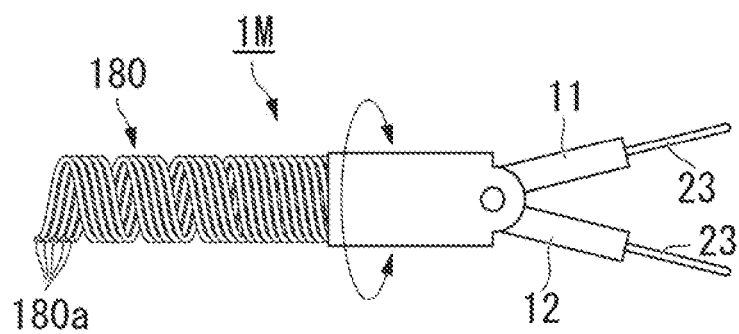
FIG. 70 is a schematic side view showing a portion of an endoscopic device according to a twelfth embodiment of the present invention.

Next, an endoscopic device 1M of a twelfth embodiment of the present invention will be described. FIG. 70 is a schematic side view showing a portion of the endoscopic device according to the embodiment.

As shown in FIG. 70, the endoscopic device 1M of the embodiment has a coil sheath 180 constituted by many sets of coils, instead of the longitudinal member 3 described in the first embodiment.

The coil sheath 180 is a coil formed in a cylindrical shape in which a plurality of element wires 180a are wound to form a spiral shape in a state the plurality of element wires 180a are adjacent to each other to form a spiral shape in a state in which the plurality of element wires 180a are adjacent to each other. In the embodiment, the coil sheath 180 has five element wires 180a parallel to each other and adhered to each other. Further, in FIG. 70, a gap between the element wires 180a is shown as an empty space such that it can be apparent that many sets of coils are constituted by the element wires 180a. In the embodiment, the plurality of element wires 180a that constitute the coil sheath 180 have equal radiuses to each other when the element wires are wound in a coil shape. That is, the coil sheath 180 is a single layer coil in a coil diameter direction of the coil sheath 180. The number of element wires 180a used in the coil sheath 180 is not particularly limited as long as the number is two or more. For example, the number of element wires 180a used in the coil sheath 180 is selected in consideration of a balance of transmission characteristics of a compressive force in a centerline direction of a coil of the coil sheath 180 and transmission characteristics of a rotational force in a circumferential direction of a coil of the coil sheath 180. That is, in the coil sheath 180, the rotational force can be efficiently transmitted when the plurality of element wires 180a are provided, in comparison with the case in which one element wire 180a is provided.

Further, in the first embodiment and the second embodiment, linear members that constitute the first grasping members 21 and 41 and the second grasping members 22 and 42 may not be constituted by wires having flexibility.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. An endoscopic device comprising:
   a longitudinal member having a longitudinal axis;
   a first jaw and a second jaw provided at a distal end of the longitudinal member, the first jaw and the second jaw being configured to freely rotate around an intersecting axis extending in a direction intersecting the longitudinal axis of the longitudinal member such that the first jaw and the second jaw open and close;
   an operating transmission member elongated along the longitudinal axis of the longitudinal member, the operating transmission member being linked with the first jaw and the second jaw, the operating transmission member being installed to be movable along the longitudinal axis of the longitudinal member;
   a first wire member inserted into the first jaw, the first wire member being elastically deformable; and
   a second wire member inserted into the second jaw, the second wire member being elastically deformable, wherein
   the first jaw includes a first wall surface that forms a first through-hole elongated along a longitudinal axis of the first jaw, the first through-holes has: (i) a first distal end opening formed at a distal end of the first jaw, and (ii) a first proximal end opening formed between the first distal end opening and the intersecting axis in the longitudinal axis of the first jaw,
   the first wire member includes:
      a first loop portion that is configured to protrude from the first distal end opening, the first loop portion forming a first tissue grasping surface having a looped shape, the first loop portion being engaged with the first wall surface of the first jaw in a first rotation direction around the longitudinal axis of the first jaw, and
      a first proximal portion that connects the first loop portion, the first proximal portion protruding from the first proximal end opening,
   the second jaw includes a second wall surface that forms a second through-hole elongated along a longitudinal axis of the second jaw, the second through-hole has: (i) a second distal end opening formed at a distal end of the second jaw, and (ii) a second proximal end opening formed between the second distal end opening and the intersecting axis in the longitudinal axis of the second jaw,
   the second wire member includes:
      a second loop portion that is configured to protrude from the second distal end opening, the second loop portion forming a second tissue grasping surface having a looped shape, the second loop portion being engaged with the second wall surface of the second jaw in a second rotation direction around the longitudinal axis of the second jaw, and
      a second proximal portion that connects the second loop portion, the second proximal portion protruding from the second proximal end opening, and
   when the jaws are closed, the first loop portion is engaged with the first wall surface and the second loop portion is engaged with the second wall surface such that the first tissue grasping surface faces the second tissue grasping surface.

2. The endoscopic device according to claim 1, wherein the first tissue grasping surface of the first wire member is configured to protrude from the first jaw.

3. The endoscopic device according to claim 2, wherein the first wire member and the second wire member are installed so as to be configured to independently vary: (i) a grasping area of the first tissue grasping surface of the first wire member, and (ii) a grasping area of the second tissue grasping surface of the second wire member on a plane crossing an open-close direction of the first jaw and the second jaw according to an advance and retreat motion of the first wire member and the second wire member.

4. The endoscopic device according to claim 3, wherein
a first distal end opening portion configured to accommodate the first tissue grasping surface of the first wire member is formed at a distal end surface of the first jaw, and
a second distal end opening portion configured to accommodate the second tissue grasping surface of the second wire member is formed at a distal end surface of the second jaw.

5. The endoscopic device according to claim 3, wherein when the first wire member and the second wire member are closed, the first tissue grasping surface of the first wire member is inclined in an approaching direction with respect to the second wire member from a proximal end to a distal end of the first tissue grasping surface of the first wire member.

6. The endoscopic device according to claim 5, wherein when the first wire member and the second wire member are closed, the second tissue grasping surface of the second wire member is inclined in an approaching direction with respect to the first wire member from a proximal end to a distal end of the second tissue grasping surface of the second wire member, and one of the first wire member and the second wire member is set to enter a space inside of a curved portion of the other wire member.

7. The endoscopic device according to claim 3, wherein both ends of the first wire member and the second wire member are inserted through two through-holes formed in distal end surfaces of each of the first jaw and the second jaw, the ends of the first wire member and the second wire member are extended toward the longitudinal member, and the ends of the first wire member and the second wire member are installed so as to advance in a direction protruding from the first jaw and the second jaw and retreat in a direction accommodated in the first jaw and the second jaw.

8. The endoscopic device according to claim 7, wherein the first wire member includes a main wire and an auxiliary wire, the auxiliary wire having a smaller grasping area than a grasping area of the main wire, the auxiliary wire being disposed inside the main wire at intervals.

9. The endoscopic device according to claim 2, wherein the first wire member and the second wire member each have main wires and auxiliary wires, the auxiliary wires have a smaller grasping area than a grasping area of the main wires, and the auxiliary wires are disposed inside the respective main wires at intervals, and
the grasping area of the auxiliary wire of the first wire member and the grasping area of the auxiliary wire of the second wire member are different from each other.

10. The endoscopic device according to claim 9, wherein a centerline of each of the main wires connecting between a point where each of the main wires is supported by the first jaw and the second jaw and a point that is maximally spaced apart from the first jaw and the second jaw, and a centerline of each of the auxiliary wires connecting between a point where each of the auxiliary wires is supported by the first jaw and the second jaw and a point that is maximally spaced apart from the first jaw and the second jaw, are positioned so as to overlap in a same plane including both of the main wires and the auxiliary wires.

11. The endoscopic device according to claim 9, wherein a centerline of each of the main wires connecting between a point where each of the main wires is supported by the first jaw and the second jaw and a point that is maximally spaced apart from the first jaw and the second jaw, and a centerline of each of the auxiliary jaws connecting between a point where each of the auxiliary wires supported by the first jaw and the second jaw and a point that is maximally spaced apart from the first jaw and the second jaw, are deviated from each other when viewed in a direction perpendicular to a plane including the main wires.

12. The endoscopic device according to claim 9, wherein when the first wire member and the second wire member are closed, tissue grasping surfaces of the main wire and the auxiliary wire of the first wire member are set to be inclined in an approaching direction with respect to the second wire member from a proximal end to a distal end of the tissue grasping surfaces of the main wire and the auxiliary wire of the first wire member, and tissue grasping surfaces of the main wire and the auxiliary wire of the second wire member are set to be inclined in an approaching direction with respect to the first wire member from a proximal end to a distal end of the tissue grasping surfaces of the main wire and the auxiliary wire of the second wire member.

13. The endoscopic device according to claim 12, wherein at least one of the main wires and the auxiliary wires of the first wire member is set to enter a space inside a curved portion of at least one of the main wires and the auxiliary wires of the second wire member.

14. The endoscopic device according to claim 12, further comprising an operating portion connected to at least one of the first wire member and the second wire member which are installed at a proximal end of the longitudinal member, the operating portion including:
a first movable member configured to advance and retreat the respective main wire of at least one of the first wire member and the second wire member in a central axis direction of the longitudinal member; and
a second movable member configured to advance and retreat the respective auxiliary wire of at least one of the first wire member and the second wire member in the central axis direction of the longitudinal member.

15. The endoscopic device according to claim 14, further comprising:
a first slider serving as the first movable member, the first slider being: (i) fixed to the main wire, (ii) disposed at the operating portion, and (iii) configured to advance and retreat in a predetermined direction in the operating portion;
a second slider serving as the second movable member, the second slider being: (i) fixed to the auxiliary wire, (ii) disposed at the operating portion, and (iii) configured to advance and retreat in the predetermined direction; and
a stopper installed at the first slider, the stopper being configured to limit movement of the second slider to a distal end side of the operating portion that is away the first slider, wherein
the second slider is configured to freely advance and retreat in the predetermined direction when the second slider is disposed to be spaced apart from the first slider that is away from a proximal end side of the operating portion, and
the second slider is configured to move to the proximal end side of the operating portion while abutting the stopper, and the second slider is configured to more to the distal end side of the operating portion only upon moving to the distal end side of the operating portion with the first slider.

16. The endoscopic device according to claim 14, wherein
the first movable member is a first pulley in which the respective main wire of at least one of the first wire member and the second wire member is suspended on an outer circumference of the first pulley,
the second movable member is a second pulley in which the respective auxiliary wire of at least one of the first wire member and the second wire member is suspended on an outer circumference of the second pulley,
the first pulley has a larger diameter than a diameter of the second pulley, and
the first pulley and the second pulley are integrally rotatable about a same rotational center.

17. The endoscopic device according to claim 16, further comprising:
a rotary shaft concentric with the rotational center and fixed to the first pulley and the second pulley; and
a dial installed at a portion of the rotary shaft and positioned outside the operating portion, the dial being rotated by an operator.

18. The endoscopic device according to claim 16, further comprising:
a pinion connected to the first pulley and the second pulley;
a rack meshed with the pinion and disposed in the operating portion; and
a slider formed at a portion of the rack, the slider being disposed outside the operating portion, the slider being installed to advance and retreat in a lengthwise direction of the rack by an operator.

19. The endoscopic device according to claim 1, further comprising an open-close operating portion, wherein
the first wire member is configured to protrude and retract from the first distal end opening of the first jaw, the first wire member being curved in a loop shape on a plane crossing an open-close direction of the first jaw and the second jaw,
the second wire member is configured to protrude and retract from the second distal end opening of the second jaw, the second wire member being curved in a loop shape on the plane crossing the open-close direction of the first jaw and the second jaw,
the open-close operating portion is configured to adjust a protrusion amount of the second tissue grasping surface of the second wire member from the second distal end of the second jaw so as to coincide with a grasping area of the first tissue grasping surface of the first grasping member, and
the open-close operating portion is installed at a proximal end portion of the operating transmission member, the open-close operating portion being configured to be manipulated to open and close the first jaw and the second jaw, the open-close operating portion being configured to add or release a grasping force of grasping an object to be grasped between the first tissue grasping surface of the first wire member and the second tissue grasping surface of the second wire member.

* * * * *